US011419754B2

(12) United States Patent
Vergara et al.

(10) Patent No.: US 11,419,754 B2
(45) Date of Patent: Aug. 23, 2022

(54) HEAT EXCHANGE MODULE AND SYSTEM FOR MEDICAL APPLICATIONS

(71) Applicant: THE REGENTS OF THE UNIVERSITY OF CALIFORNIA, Oakland, CA (US)

(72) Inventors: Julio L. Vergara, Los Angeles, CA (US); Andrew Padula, Laguna Niguel, CA (US); Daniel M. Estrada, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 595 days.

(21) Appl. No.: 16/136,724

(22) Filed: Sep. 20, 2018

(65) Prior Publication Data
US 2019/0099287 A1 Apr. 4, 2019

Related U.S. Application Data

(63) Continuation of application No. PCT/US2016/024592, filed on Mar. 28, 2016.

(51) Int. Cl.
*A61F 7/00* (2006.01)
*A61F 7/02* (2006.01)
(Continued)

(52) U.S. Cl.
CPC ............ *A61F 7/007* (2013.01); *A61F 7/0053* (2013.01); *A61F 7/0085* (2013.01); *A61F 7/02* (2013.01);
(Continued)

(58) Field of Classification Search
CPC ............ A61F 7/0053; A61F 2007/0075; A61F 2007/0076; A61F 2007/0056; A61F 7/007;
(Continued)

(56) References Cited

U.S. PATENT DOCUMENTS 2,991,627 A 7/1961 Suits
3,196,524 A 7/1965 Jamison
(Continued)

FOREIGN PATENT DOCUMENTS

CA 2980764 A1 10/2016
CN 101309657 A 11/2008
(Continued)

OTHER PUBLICATIONS

DE-4238291-A1 English Machine Translation (Year: 1994).*
(Continued)

*Primary Examiner* — Jenna M Hopkins
(74) *Attorney, Agent, or Firm* — O'Banion & Ritchey LLP; John P. O'Banion

(57) ABSTRACT

A heat exchange module alone or part of a system including a control console. The module includes a channel assembly and a heat exchange stack attached thereto, and can be used to directly cool and/or heat tissue or skin. The channel assembly includes a liquid channel. The stack can include a pair of spaced plates with thermoelectric coolers exchangers, heat reflective layers, and a core composite layer which keeps the plates spaced. To provide flexibility of the module to better fit on round body parts the stack can include a thermally-conductive plate construction between the plates which has rotational flexibility axes in the X and/or Y directions between plate portions. Optionally the channel can include windows to which the plate portions are sealed. The heat exchange stack separately or together with the channel assembly can be secured in the thickness direction with mechanical securements such as sewing or tacking to also provide for greater flexibility.

20 Claims, 19 Drawing Sheets

(51) Int. Cl.
*F25B 21/04* (2006.01)
*F25B 21/02* (2006.01)

(52) U.S. Cl.
CPC ............ *A61F 2007/0008* (2013.01); *A61F 2007/0039* (2013.01); *A61F 2007/0054* (2013.01); *A61F 2007/0056* (2013.01); *A61F 2007/0075* (2013.01); *A61F 2007/0076* (2013.01); *A61F 2007/0225* (2013.01); *A61F 2007/0246* (2013.01); *F25B 21/02* (2013.01); *F25B 21/04* (2013.01); *F25B 2321/02* (2013.01); *F25B 2321/023* (2013.01); *F25B 2321/0252* (2013.01)

(58) Field of Classification Search
CPC .. A61F 7/0085; A61F 7/02; A61F 2007/0008; A61F 2007/0039; A61F 2007/0054; A61F 2007/00225; A61F 2007/0246; A61F 2007/0225; A61F 2007/0246; F25B 21/02; F25B 21/04; F25B 2321/02; F25B 2321/023; F25B 2321/0252
See application file for complete search history.

(56) References Cited

U.S. PATENT DOCUMENTS

| | | | |
|---|---|---|---|
| 3,867,939 A * | 2/1975 | Moore | A61F 7/02 607/104 |
| 4,470,263 A | 9/1984 | Lehovec | |
| 4,846,176 A * | 7/1989 | Golden | A61F 7/02 607/104 |
| 4,860,748 A | 8/1989 | Chiurco | |
| 4,962,761 A * | 10/1990 | Golden | A61F 7/02 165/46 |
| 5,097,829 A * | 3/1992 | Quisenberry | A61F 7/02 219/490 |
| 5,174,285 A | 12/1992 | Fontenot | |
| 5,584,183 A | 12/1996 | Wright | |
| 5,603,728 A | 2/1997 | Pachys | |
| 5,653,741 A | 8/1997 | Grant | |
| 5,800,490 A | 9/1998 | Patz | |
| 5,871,526 A | 2/1999 | Gibbs | |
| 5,887,435 A | 3/1999 | Morton | |
| 5,895,418 A | 4/1999 | Saringer | |
| 5,899,077 A * | 5/1999 | Wright | H01L 35/32 62/3.7 |
| 6,019,783 A | 2/2000 | Philips | |
| 6,205,790 B1 | 3/2001 | Denkin | |
| 6,375,674 B1 | 4/2002 | Carson | |
| 6,739,138 B2 | 5/2004 | Saunders | |
| 6,764,502 B2 * | 7/2004 | Bieberich | A61F 7/10 607/104 |
| 6,840,955 B2 | 1/2005 | Ein | |
| 7,022,093 B2 * | 4/2006 | Smith | A61F 5/0106 602/14 |
| 7,077,858 B2 * | 7/2006 | Fletcher | A61F 7/02 607/104 |
| 7,637,263 B2 * | 12/2009 | Fisher | A61F 7/03 128/898 |
| 7,666,215 B2 * | 2/2010 | Callister | G05D 23/1925 607/105 |
| 7,959,657 B1 | 6/2011 | Harsy | |
| 8,065,763 B2 | 11/2011 | Brykalski | |
| 8,192,474 B2 * | 6/2012 | Levinson | A61F 7/007 607/96 |
| 8,283,602 B2 * | 10/2012 | Augustine | A61F 7/007 219/212 |
| 9,078,478 B2 * | 7/2015 | Ross, Jr. | A61B 5/1114 |
| 9,132,031 B2 * | 9/2015 | Levinson | A61F 7/0085 |
| 9,278,023 B2 * | 3/2016 | Dabrowiak | A61F 7/007 |
| 9,421,123 B2 * | 8/2016 | Lee | A61N 1/36021 |
| 9,962,284 B2 * | 5/2018 | Robinson | A61F 7/02 |
| 10,292,859 B2 | 5/2019 | Levinson | |
| 10,449,726 B2 * | 10/2019 | Vergara | B29C 66/53461 |
| 11,240,882 B2 * | 2/2022 | Inaba | B60N 2/5692 |
| 2002/0026226 A1 | 2/2002 | Ein | |
| 2002/0120317 A1 | 8/2002 | Fletcher | |
| 2002/0156509 A1 | 10/2002 | Cheung | |
| 2002/0161419 A1 | 10/2002 | Carson | |
| 2003/0097845 A1 | 5/2003 | Saunders | |
| 2004/0158303 A1 | 8/2004 | Lennox | |
| 2004/0159109 A1 * | 8/2004 | Harvie | A41D 13/0051 62/3.5 |
| 2005/0065581 A1 * | 3/2005 | Fletcher | F28F 3/12 607/104 |
| 2005/0143797 A1 | 6/2005 | Parish | |
| 2006/0280948 A1 | 12/2006 | Moreshead | |
| 2006/0293732 A1 | 12/2006 | Collins | |
| 2008/0046047 A1 | 2/2008 | Jacobs | |
| 2008/0077201 A1 * | 3/2008 | Levinson | A61B 5/6843 607/96 |
| 2008/0077211 A1 * | 3/2008 | Levinson | A61F 7/10 607/108 |
| 2008/0097560 A1 | 4/2008 | Radziunas | |
| 2008/0097562 A1 * | 4/2008 | Tan | A61M 5/44 607/113 |
| 2008/0188915 A1 | 8/2008 | Mills | |
| 2008/0249524 A1 * | 10/2008 | Dunning | A61B 18/16 606/41 |
| 2008/0287839 A1 * | 11/2008 | Rosen | A61H 7/008 601/18 |
| 2009/0000309 A1 | 1/2009 | Hershberger | |
| 2009/0155838 A1 | 6/2009 | Hale | |
| 2009/0264969 A1 * | 10/2009 | Gammons | A61F 7/02 607/104 |
| 2009/0312822 A1 * | 12/2009 | Besner | A61F 7/007 607/100 |
| 2010/0132930 A1 | 6/2010 | Izenson | |
| 2010/0198322 A1 | 8/2010 | Joseph | |
| 2010/0280581 A1 * | 11/2010 | Cushman | A61F 7/03 607/112 |
| 2011/0030754 A1 | 2/2011 | Smythe | |
| 2011/0071603 A1 * | 3/2011 | Moore | A61F 7/007 607/96 |
| 2011/0238050 A1 | 9/2011 | Allison | |
| 2012/0118344 A1 | 5/2012 | Schluck | |
| 2012/0239123 A1 * | 9/2012 | Weber | A61F 7/02 607/104 |
| 2013/0013033 A1 | 1/2013 | Lowe | |
| 2013/0085552 A1 | 4/2013 | Mandel | |
| 2013/0123887 A1 * | 5/2013 | Iwanami | A61F 7/0085 607/104 |
| 2013/0172829 A1 | 7/2013 | Badawi | |
| 2014/0222121 A1 * | 8/2014 | Spence | A61F 7/02 607/104 |
| 2014/0228918 A1 | 8/2014 | Brienza | |
| 2014/0276257 A1 | 9/2014 | Santa Maria | |
| 2014/0311543 A1 | 10/2014 | Takahiro | |
| 2014/0326287 A1 * | 11/2014 | Wiant | H01L 35/32 136/205 |
| 2014/0352325 A1 * | 12/2014 | Brown | F25B 21/02 62/3.2 |
| 2015/0080989 A1 | 3/2015 | Mohn | |
| 2015/0223971 A1 | 8/2015 | Zaveri | |
| 2015/0238349 A1 * | 8/2015 | Giuliani | A61F 7/00 602/2 |
| 2015/0366703 A1 * | 12/2015 | Du | A61F 7/007 607/104 |
| 2016/0035957 A1 | 2/2016 | Casey | |
| 2016/0178251 A1 | 6/2016 | Johnson | |
| 2016/0270952 A1 | 9/2016 | Vergara | |
| 2017/0027053 A1 | 1/2017 | Moczygemba | |
| 2018/0098903 A1 * | 4/2018 | Vergara | A61F 7/0085 |
| 2018/0204993 A1 | 7/2018 | Himmer | |
| 2019/0099287 A1 * | 4/2019 | Vergara | A61F 7/007 |

(56) References Cited

U.S. PATENT DOCUMENTS

| | | | | |
|---|---|---|---|---|
| 2019/0099288 A1* | 4/2019 | Vergara | | A61F 7/007 |
| 2019/0262169 A1* | 8/2019 | Vergara | | A61F 7/08 |

FOREIGN PATENT DOCUMENTS

| | | | | |
|---|---|---|---|---|
| CN | 103142217 | A | 6/2013 | |
| CN | 203341808 | U | 12/2013 | |
| DE | 4238291 | A1 * | 5/1994 | A61F 7/10 |
| DE | 202006020386 | U1 | 7/2008 | |
| EP | 3278047 | A1 | 2/2018 | |
| JP | H04077915 | | 7/1992 | |
| JP | H04077915 | Y | 7/1992 | |
| JP | 2003323219 | | 11/2003 | |
| JP | 2006230761 | | 9/2006 | |
| JP | 2006230761 | A | 9/2006 | |
| JP | 2008546510 | A | 12/2008 | |
| JP | 2009501067 | A | 1/2009 | |
| JP | 2010515481 | | 5/2010 | |
| JP | 2011067638 | | 4/2011 | |
| KR | 1020080060193 | | 1/2008 | |
| KR | 1020140140617 | | 12/2014 | |
| KR | 20150083559 | A | 7/2015 | |
| SU | 1179987 | A1 | 9/1985 | |
| TW | 201110282 | A | 3/2011 | |
| WO | 0195841 | A2 | 12/2001 | |
| WO | 0195841 | A3 | 12/2001 | |
| WO | 02064069 | A2 | 8/2002 | |
| WO | 2004111741 | A1 | 12/2004 | |
| WO | 2007005073 | A2 | 1/2007 | |
| WO | 2008039556 | A1 | 4/2008 | |
| WO | 2008039557 | | 4/2008 | |
| WO | 2008039557 | A1 | 4/2008 | |
| WO | 2008085162 | A1 | 7/2008 | |
| WO | 2011156643 | A1 | 12/2011 | |
| WO | 2013124866 | A2 | 8/2013 | |
| WO | 2013144008 | A1 | 10/2013 | |
| WO | 2014001789 | A1 | 1/2014 | |
| WO | 2014057450 | A1 | 4/2014 | |
| WO | 2015048170 | | 4/2015 | |
| WO | 2015048170 | A | 4/2015 | |
| WO | 2015048170 | A1 | 4/2015 | |
| WO | 2016160691 | | 10/2016 | |
| WO | 2016160691 | A1 | 10/2016 | |
| WO | 2017171719 | | 10/2017 | |
| WO | 2017171719 | A1 | 10/2017 | |
| WO | 2017172836 | | 10/2017 | |
| WO | 2018064220 | A1 | 4/2018 | |
| WO | 2018064428 | | 4/2018 | |
| WO | 2018064428 | A1 | 4/2018 | |

OTHER PUBLICATIONS

Intellectual Property India, Examination Report dated Jan. 24, 2020, related India patent application No. 201647009683, pp. 1-6, claims examined, pp. 7-10.
Japan Patent Office (JPO), official action dated Apr. 21, 2020, related Japanese patent application No. 2016-517424, pp. 1-4, English-language translation pp. 5-8, claims examined pp. 9-12.
State Intellectual Property Office of the People's Republic of China, The Second Office Action dated Mar. 26, 2020, related Chinese patent application No. 201680019132.6, pp. 1-9, English-language translation, pp. 10- 24, claims examined, pp. 25-32.
Japan Patent Office (JPO), official action dated Mar. 10, 2020, related Japanese patent application No. 2017-549684, pp. 1-5, English-language translation , pp. 6-10, claims examined, pp. 11-16.
Korean Intellectual Property Office (KIPO), official action dated Mar. 9, 2020, related Korean patent application No. 10-2017-7030302, pp. 1-7, English-language translation, pp. 8-10, claims examined, pp. 11-16.
Japan Patent Office (JPO), official action dated Mar. 17, 2020, related Japanese patent application No. 2018-550772, pp. 1-7, English-language translation, pp. 8-15, claims examined, pp. 16-19.
National Intellectual Property Administration, PRC (CNIPA), The First Office Action dated Jul. 3, 2019, related China Patent Application No. 201680019132.6, Chinese-language document pp. 1-9, English-language translation p. 10-21, claims examined pp. 22-27.
IPEA/US, United States Patent and Trademark Office (USPTO), International Preliminary Report on Patentability dated Sep. 10, 2018, related PCT international application No. PCT/US2016/024592, pp. 1-12, claims, pp. 13-20, drawings, pp. 21-46, Article 34 amendment, pp. 47-56.
IP Australia, Examination report No. 2 dated Dec. 6, 2018, related Australian patent application No. 2014326780, pp. 1-7, claims examined, pp. 8-11.
Japan Patent Office (JPO), Decision of Refusal dated Dec. 11, 2018, related Japanese patent application No. 2016-517424, Japanese-language document pp. 1-6, English-language translation pp. 7-11, claims examined pp. 12-15.
European Patent Office (EPO), Communication {Extended European Search Report) dated Oct. 18, 2018, related European patent application No. 16773916.8, pp. 1-9, claims searched, pp. 10-12.
IPEA/US, United States Patent and Trademark Office, International Preliminary Report on Patentability dated Mar. 8, 2019, related PCT international application No. PCT/US2017/024628, pp. 1-9, claims examined, pp. 10-34.
European Patent Office (EPO), Communication (extended European search report) dated Apr. 8, 2020, related European patent application No. EP 17857465.3, pp. 1-8, claims searched, pp. 9-11.
Korean Intellectual Property Office (KIPO), International Search Report and Written Opinion, counterpart PCT international patent application No. PCT/US2014/057276, dated Jan. 8, 2015, pp. 1-17, with claims searched, pp. 18-21.
European Patent Office (EPO), extended European search report dated Mar. 29, 2017, related European patent application No. 14849500.5, pp. 1-8, with claims searched, pp. 9-11.
ISA/US, United States Patent and Trademark Office (USPTO), International Search Report and Written Opinion dated Jul. 1, 2016, related PCT international application No. PCT/US2016/024501, pp. 1-19, with claims searched, pp. 20-25.
ISA/US, United States Patent and Trademark Office (USPTO), International Search Report and Written Opinion dated Sep. 14, 2016, related PCT international application No. PCT/US2016/024592, pp. 1-13, with claims searched, pp. 14-17.
IP Australia, Patent Examination Report 1 dated May 24, 2018, related Australian patent application No. 2014326780, pp. 1-4, with claims examined, pp. 5-7.
ISA/US, United States Patent and Trademark Office (USPTO), International Search Report and Written Opinion dated Aug. 28, 2017, related PCT international application No. PCT/US2017/024628, pp. 1-23, with claims searched, pp. 24-46.
ISA/US, United States Patent and Trademark Office (USPTO), International Search Report and Written Opinion dated Mar. 8, 2018, related PCT international application No. PCT/US2017/053812, pp. 1-16, with claims searched, pp. 17-35.
ISA/US, United States Patent and Trademark Office (USPTO), International Search Report and Written Opinion dated Feb. 6, 2018, related PCT international application No. PCT/US2017/054196, pp. 1-18, with claims searched, pp. 19-32.
Japan Patent Office (JPO), official action dated Jul. 31, 2018, related Japanese patent application No. 2016-517424, Japanese-language document pp. 1-6, English-language translation pp. 7-12, claims examined pp. 13-16.
Japan Patent Office (JPO), official action dated Jun. 16, 2020, related Japanese patent application No. 2019-074530, pp. 1-7, English-language translation (partial), pp. 8-12, claims examined, pp. 13-17.
Korean Intellectual Property Office (KIPO), official action dated Jun. 4, 2020, related Korean patent application No. 10-2018-7028057, pp. 1-4, English-language translation, pp. 5-7, claims examined, pp. 8-11.
State Intellectual Property Office of the People's Republic of China, The First Office Action dated Jul. 29, 2020, related Chinese patent application No. 201780020778.0, pp. 1-14, English-language translation, pp. 15-33, claims examined, pp. 34-58.

(56) References Cited

OTHER PUBLICATIONS

IP Australia, Examination report No. 1 for standard patent application dated Aug. 26, 2020, related Australian patent application No. 2016243565, pp. 1-5, claims examined, pp. 6-11.
IPEA/US, United States Patent and Tradmark Office (USPTO), International Preliminary Report on Patentability dated Oct. 21, 2019, related PCT international application No. PCT/US2017/054196, pp. 1-16, claims, pp. 17-45, Article 34 amendment, pp. 46-53.
European Patent Office (EPO), Communication (extended European search report) dated Sep. 25, 2019, related European patent application No. EP 16897277.6, pp. 1-9, claims searched, pp. 10-12.
European Patent Office (EPO), Communication (extended European search report) dated Oct. 22, 2019, related European patent application No. EP 17776506.2, pp. 1-12, claims searched, pp. 13-15.
European Patent Office (EPO), Communication pursuant to Article 94(3) EPC dated Jun. 1, 2021, related European patent application No. 14 849 500.5, pp. 1-6, claims examined, pp. 7-10.
Korean Intellectual Property Office, Notice of Preliminary Rejection dated Jul. 16, 2021, related Korean patent application No. 10-2018-7028696, pp. 1-7, English-language translation, pp. 8-11, claims examined, pp. 12-24.
Japan Patent Office (JPO), official action dated Aug. 31, 2021, related Japanese patent application No. 2019-516508, pp. 1-6, English-language translation, pp. 7-12, claims examined, pp. 13-20.
Canadian Intellectual Property Office, office action dated Dec. 29, 2020, related Canadian patent application No. 2,925,094, pp. 1-8, claims examined, pp. 9-12.
European Patent Office (EPO), Communication pursuant to Article 94(3) EPC dated Dec. 12, 2020, repated European patent application No. EP 16773916.8, pp. 1-8, claims examined, p. 9-10.
Japan Patent Office, official action dated Jan. 5, 2021, related Japanese patent application No. 2017-549684, pp. 1-4, English-language translation, pp. 5-7, claims examined, pp. 8-12.
Korean Intellectual Property Office, official action dated Jan. 11, 2021, prepared Korean patent application No. 10-2016-7007807, pp. 1-11, English-language translation, pp. 12-14, claimls examined, pp. 15-18.

P Australia, Examination report No. 2 for standard patent application dated Aug. 26, 2020, related Australian patent application No. 2016243565, pp. 1-6, claims examined, pp. 7-11.
The Patent Office of the People's Repubic of China, official action dated Jan. 12, 2021, related Chinese patent application No. 2017800664983, pp. 1-6, Englis-language translation, pp. 7-15, claims examined, pp. 16-29.
State Intellectual Property Office of the People's Republic of China, The Third Office Action dated Feb. 28, 2022, related Chinese patent application No. 201780066498.3, pp. 1-3, English-language translation, pp. 4-8, claims examined, pp. 5-13.
State of Israel Ministry of Justice the Patent Authority, Notification No. 26, issued Dec. 1, 2021, related Israel patent application No. 265686, pp. 1-4, English-language translation, pp. 5-8, claims examined, pp. 9-19.
Japan Patent Office (JPO), official action dated Dec. 20, 2021, related Japanese patent application No. 2018-551821, pp. 1-3, English-language translation pp. 4-6, claims examined, pp. 7-35.
The Patent Office of the People's Repubic of China, official action dated Jan. 6, 2022, related Chinese patent application No. 201680084088.7, pp. 1-10, English-language machine translation, pp. 11-19, claims examined, pp. 20-23.
Korean Intellectual Property Office, official action dated Feb. 16, 2022, related Korean patent application No. 10-2019-7009157, pp. 1-7, English-language translation, pp. 8-11, claims examined, pp. 12-25.
IP Australia, Examination report No. 1 for standard patent application dated Feb. 21, 2022, related Australian patent application No. 2017335975, pp. 1-5, claims examined, pp. 6-19.
Japan Patent Office (JPO), official action dated May 10, 2022, related Japanese patent application No. 2019-516508, pp. 1-3, English-language translation, pp. 4-6, claims examined, pp. 7-13.
Canadian Intellectual Property Office, office action dated May 27, 2022, related Canadian patent application No. 2,980,764, pp. 1-3, claims examined, pp. 4-9.

\* cited by examiner

HEAT EXCHANGE MODULE AND SYSTEM FOR MEDICAL APPLICATIONS

CROSS-REFERENCE TO RELATED APPLICATIONS

This application claims priority to, and is a 35 U.S.C. § 111(a) continuation of, PCT international application number PCT/US2016/024592 filed on Mar. 28, 2016, incorporated herein by reference in its entirety, which was published as PCT International Publication No. WO 2017/171719 A1 on Oct. 5, 2017, incorporated herein by reference in its entirety.

This application is related to PCT international application number PCT/US2014/057276 filed on Sep. 24, 2014, incorporated herein by reference in its entirety, which was published as PCT International Publication No. WO 2015/048170 A1 on Apr. 2, 2015, incorporated herein by reference in its entirety, and which claims priority to, and the benefit of, U.S. provisional patent application Ser. No. 61/884,932 filed on Sep. 30, 2013, incorporated herein by reference in its entirety.

This application is related to PCT international application number PCT/US2016/024501 filed on Mar. 28, 2016, incorporated herein by reference in its entirety, which was published as PCT International Publication No. WO 2016/160691 A1 on Oct. 6, 2016, incorporated herein by reference in its entirety, and which claims priority to, and the benefit of, U.S. provisional patent application Ser. No. 62/139,676 filed on Mar. 28, 2015, incorporated herein by reference in its entirety.

This application is related to PCT international application number PCT/US2017/024628 filed on Mar. 28, 2017, incorporated herein by reference in its entirety, which was published as PCT International Publication No. WO 2017/172836 A1 on Oct. 5, 2017, incorporated herein by reference in its entirety, and which claims priority to, and the benefit of, U.S. provisional patent application Ser. No. 62/400,836 filed on Sep. 28, 2016, incorporated herein by reference in its entirety, and which also claims priority to, and the benefit of, PCT international application number PCT/US2016/024592 filed on Mar. 28, 2016, incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

The technology of this disclosure pertains generally to flexible heat exchange modules (HEMs) that contain thermoelectric coolers (TECs) and can be used for heating or cooling. Hypothermia treatment of patients is used for a variety of applications, including but not limited to treatment of brain injuries, spinal cord injuries, muscle injuries, and joint injuries. This treatment is typically afforded by using ice packs or chemical cool packs that provide incomplete and short-lived cooling. For more advanced treatments, such as treatment of cardiac arrest and hypoxic ischemic encephalopathy, products presently available use pads or cold caps that cool by circulating chilled water.

SUMMARY

A HEM can use a pair of flexible substrates to form open channels using radio-frequency (RF) welding or similar method. The resulting channels may be used to pass a liquid to dissipate heat out of the HEM.

The liquid that is passed through the closed channels acts as a heat sink for the TECs contained within the device. Power is supplied by a controller to the TECs to induce cooling or heating.

One or more temperature sensors detect the temperature of the cooling or heating surface and may be used as feedback to the control unit. The HEM may be used for heating, cooling, or cycling between heating and cooling for various medical uses.

The HEM can include a heat exchange stack attached to a water channel assembly, both of which are discussed below according to embodiments of the disclosure.

Heat exchange stacks herein can be assemblies that allow for direct cooling and/or heating of tissue or skin. They are comprised of all the heat exchange module's components except for the water channel assembly and the biocompatible layer that interfaces with a patient's tissue or skin. In this assembly there is a cover that distributes the cooling or heating of the thermoelectric coolers which interfaces with the biocompatible layer, a core composite for interstitial insulation and structural stability, up to two sheets of reflective material to prevents radiation, at least one thermistor for temperature feedback, the thermoelectric cooler array for cooling and heating, and an additional cover or plates for heat dissipation which will be interfaced with the water channels. This last array of plates or cover is made such that there is an increased flexibility in the heat exchange stack. This assembly of components, except for the biocompatible layer unless specified for the design, can then be mechanically fastened with methods including sewing or riveting to make the heat exchange stack. The water channels may or may not already be attached for the fastening process, again depending on the design.

Water channels herein can be assemblies that create paths for fluid to pass near or against the heat exchange stack in order to dissipate the heat produced by the heat exchange stack. They can be constructed pursuant to various methods including radio frequency welded plastic films.

The present application includes a number of different definitions of the disclosures including the module or device, subassemblies of the method or device (such as the heat exchange stack and the water channels), methods of making the module or device, methods of making the subassemblies, the console, the umbilical, the overall system, methods of making the devices and subassemblies, and methods of using the devices, systems and subassemblies thereof.

Further aspects of the technology described herein will be brought out in the following portions of the specification, wherein the detailed description is for the purpose of fully disclosing preferred embodiments of the technology without placing limitations thereon.

DETAILED DESCRIPTION

1. Overview

Figure 28:
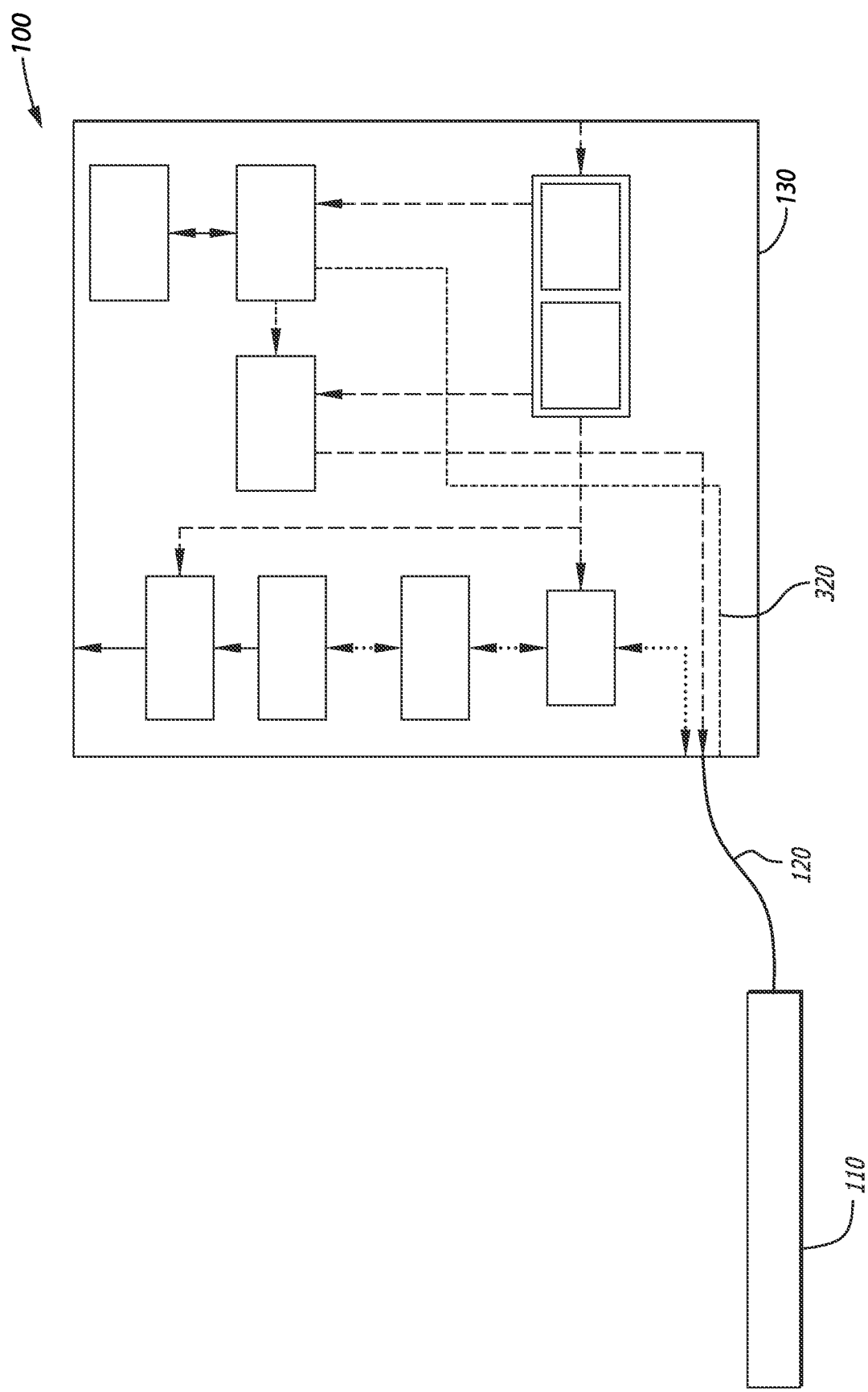
FIG. 28 and FIG. 29 show system overviews.
Figure 29:
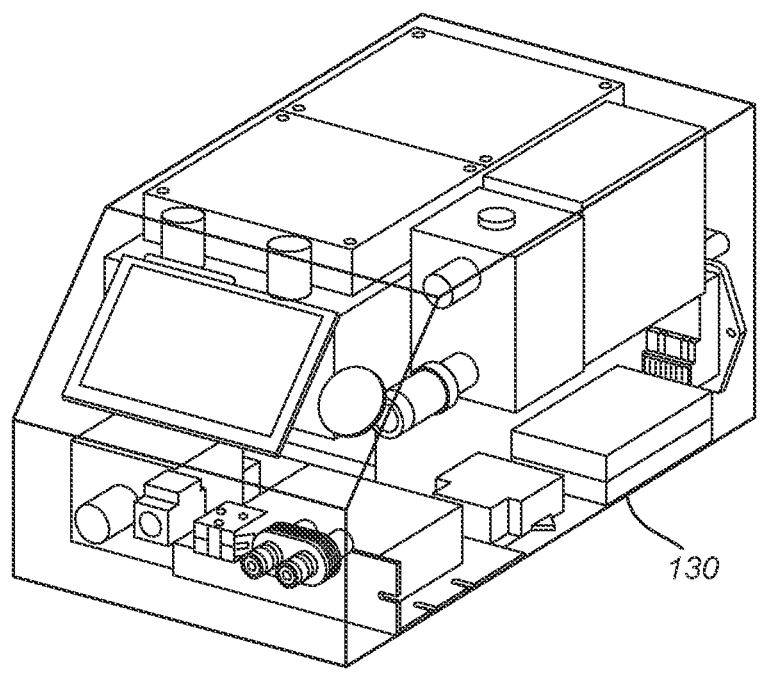
Figure 30:
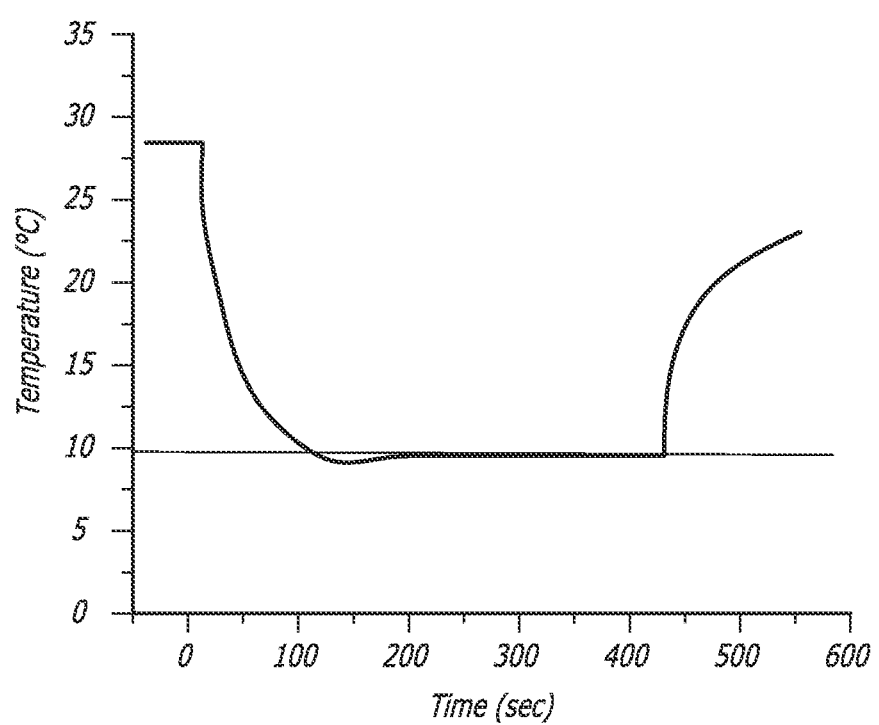
FIG. 30 and FIG. 31 are graphs showing temperature vs. time.
Figure 31:
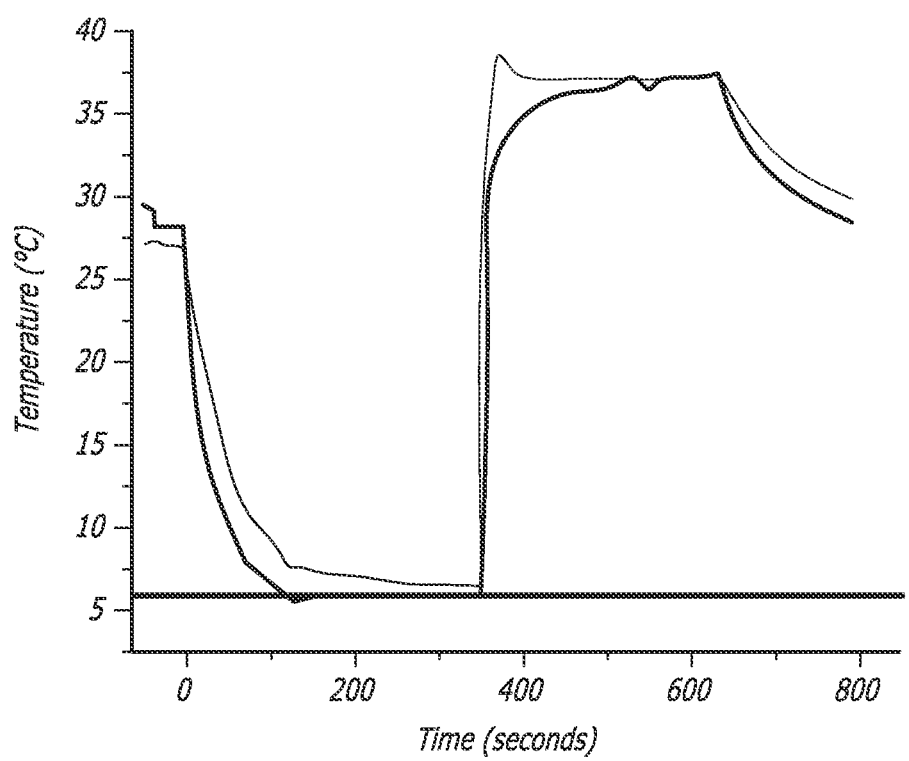

Referring to the system overviews of FIGS. 28 and 29 illustrated therein are the heat exchange systems shown generally at 100 and including a heat exchange module shown generally at 110, a console 130 and an umbilical 120 operatively connecting them. The console includes an enclosure, fans, radiator, screen drive board, touch screen, pump, jack, power/signal plug, port connector, rotary encoder, H-bridge, DC to DC power supply, reservoir, battery, USB, power outlet, flow meter, and micro-controller assembly.

Various systems of this disclosure are shown in FIGS. 1A, 1B, 1C and 1D.

FIG. 28 shows signal 320, power, fluid, and heat connections.

Figure 1A:
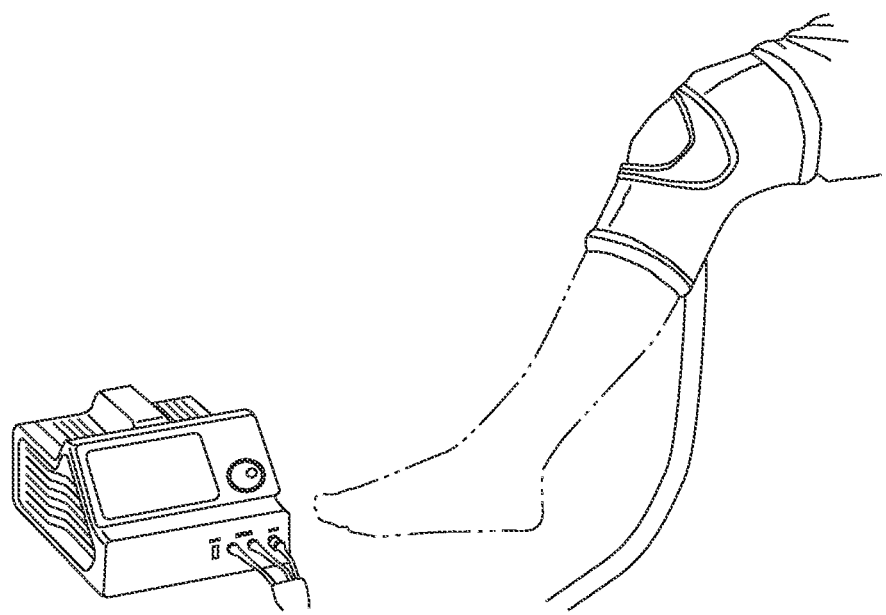
FIG. 1A is a perspective view of a system of the present disclosure shown in operation on a patient to cool and/or heat a muscle, joint and/or tissue for multiple uses, including but not limited to the treatment of sport injuries and pain management.
Figure 1B:
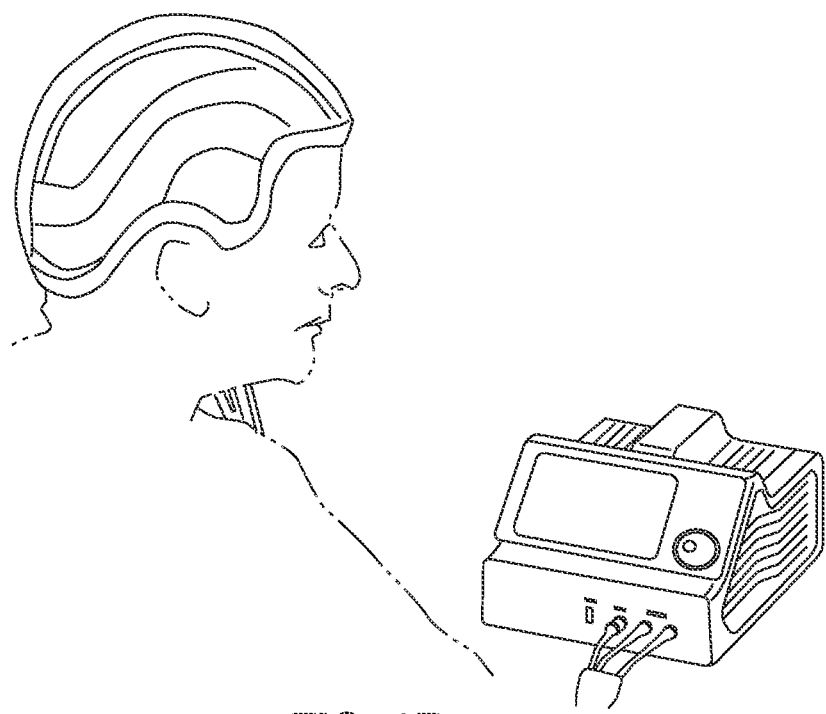
FIG. 1B is a perspective view of a system of the present disclosure shown in operation on a patient to cool and/or heat the scalp for multiple uses, including but not limited to the treatment of chemotherapy hair loss prevention.
Figure 1C:
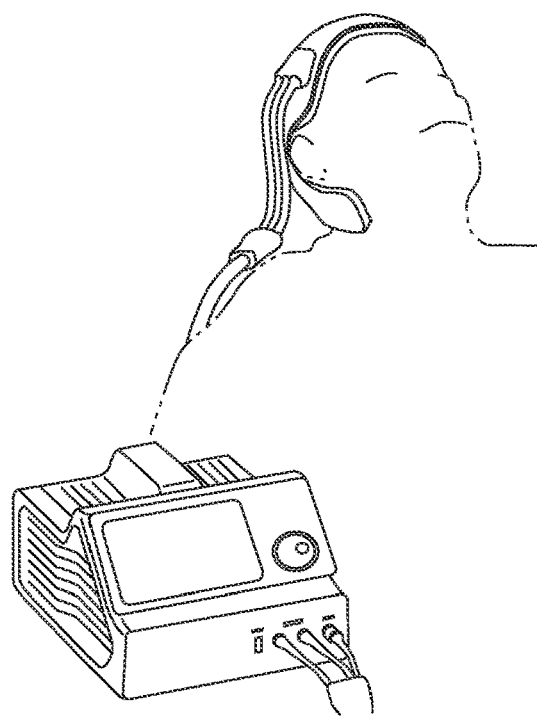
FIG. 1C is a perspective view of a system of the present disclosure shown in operation on a patient to the scalp and/or the brain for multiple uses, including but not limited to the treatment of traumatic brain injury or stroke application.
Figure 1D:
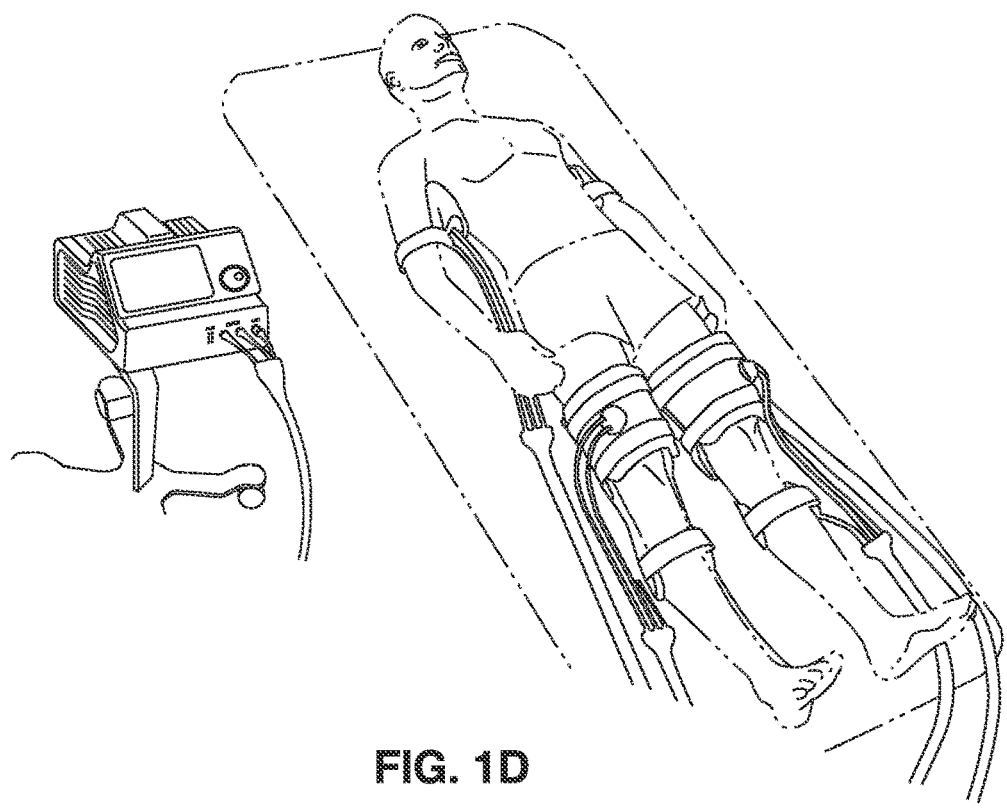
FIG. 1D is a perspective view of a system of the present disclosure shown in operation to regulate cool and/or heat core temperature of a patient for multiple uses, including but not limited to the treatment of cardiac arrest.
Figure 2:
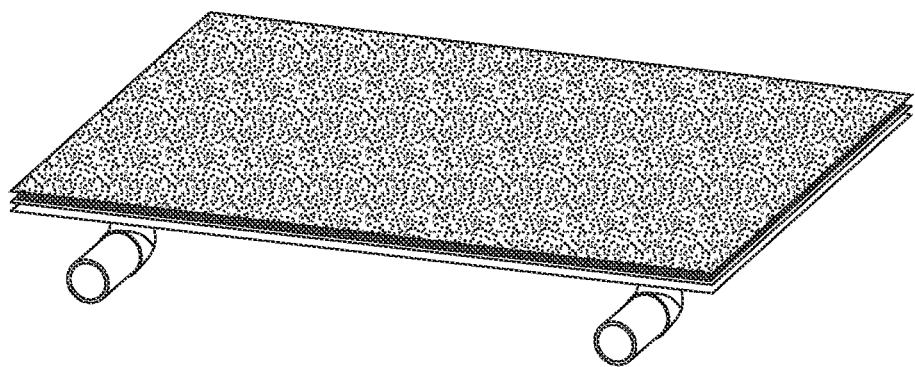
FIG. 2 is a perspective view of a heat exchange module of the present disclosure shown in isolation and such as can be used in the systems of FIGS. 1A-1D.
Figure 3:
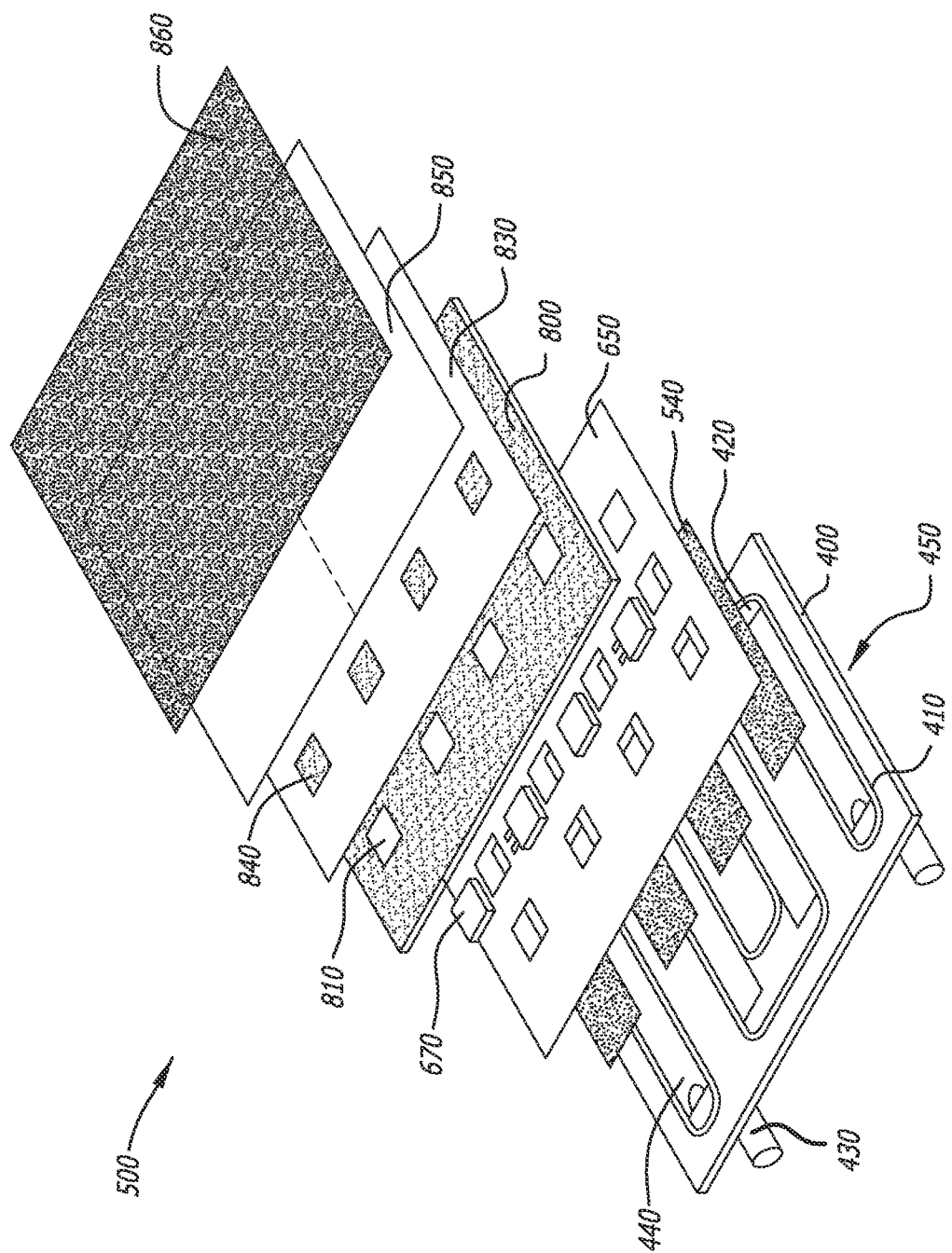
FIG. 3 is an exploded perspective view of the module of FIG. 2.

FIG. 3 is an exploded perspective view of one of the modules 110 showing the various layers including two TPU sheets 400, RF welded 410 to form a channel 420, with angled inlet and outlets 430. The channel has a plurality of windows (openings) 440 cut out to expose the interior of the channel at a plurality of locations. The sheets, channel with openings and outlet form a water channel shown generally at 450.

Figure 12A:
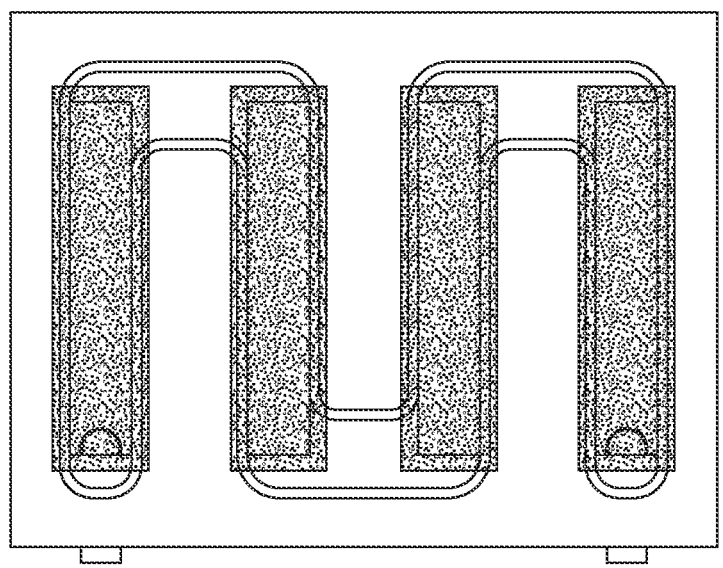
FIG. 12A is a view similar to FIG. 11 showing the plates as transparent so the backside adhesive on the plates can be seen in the channel assembly for illustrative purposes.
Figure 12B:
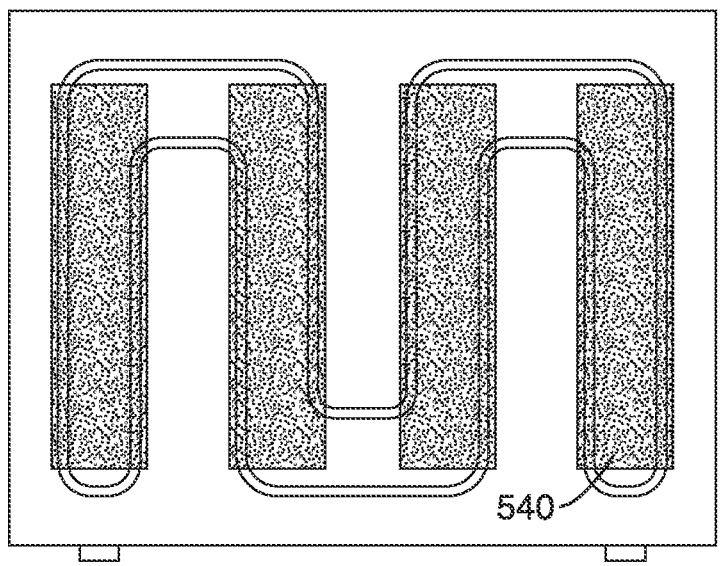
FIG. 12B is a view similar to FIG. 12A showing the backside of the channel assembly but with the alternative embodiment in which the windows are not cut out, keeping the water channel layer intact.
Figure 14:
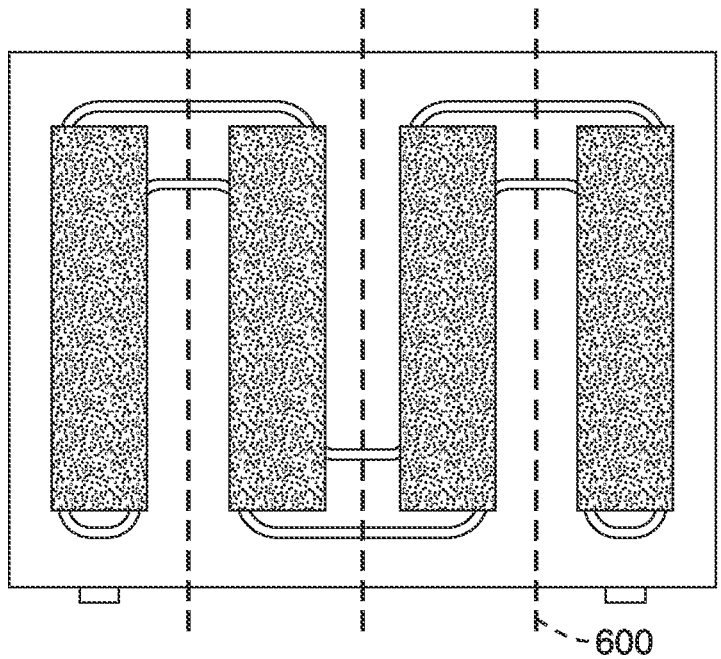
FIG. 14 is a view similar to FIG. 11 showing the axes of rotation flexibility of the channel assembly and thus of the module.
Figure 15A:
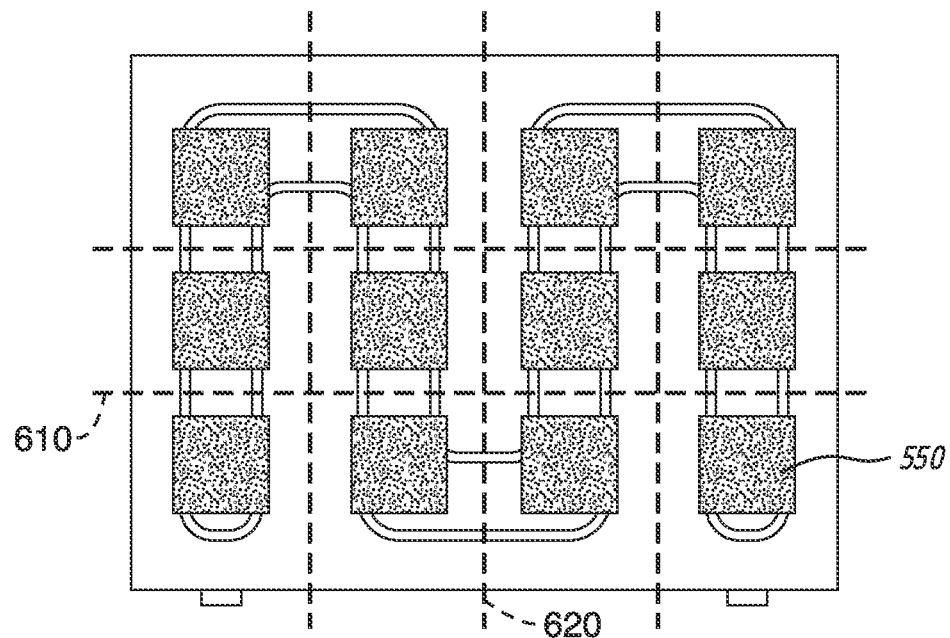
FIG. 15A is a view similar to FIG. 11 but of an alternative embodiment having twelve instead of four plates and thereby providing more axes of rotation flexibility, three in the Y direction and two in the X direction.
Figure 15B:
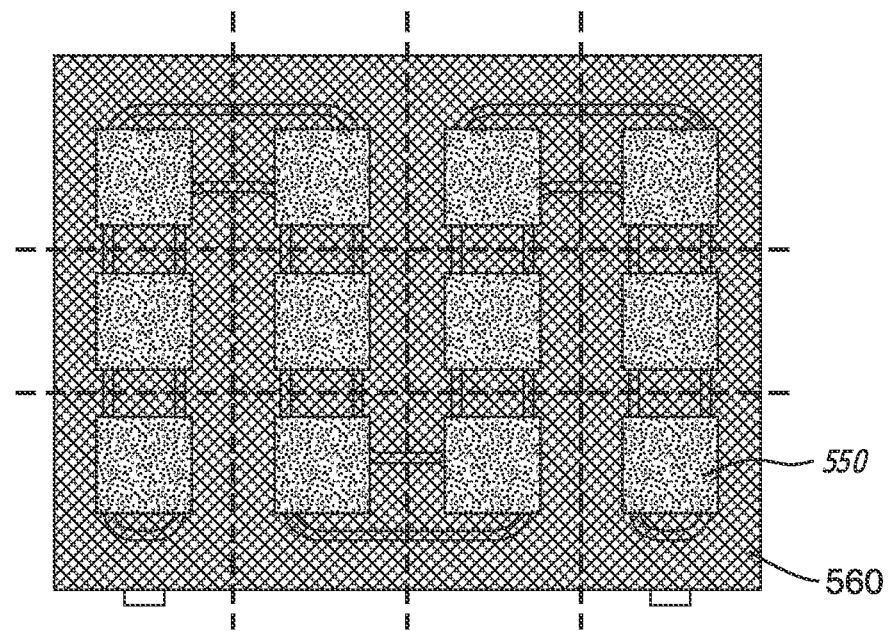
FIG. 15B is a view similar to FIG. 15A but of an alternative embodiment connecting the twelve plates with another cover illustrated by a hashed pattern.

The rest of the module forms a heat exchange stack shown generally at 500. The stack includes the bottom plates 540 collectively forming a thermally-conductive plate construction or layer. FIG. 12A shows the plates as transparent so the backside adhesive on the plates can be seen in the channel assembly for illustrative purposes. An alternative plate construction is shown in FIG. 12B where there are plates or plate pieces 540, but no windows. FIG. 15A shows an alternative embodiment having twelve instead of four plates and thereby providing more axes of rotation flexibility, three in the Y direction and two in the X direction. A further alternative is shown in FIG. 15B where the plate pieces 550 (shown in FIG. 15A and FIG. 15B) are connected together with a web. An advantage of the various plate constructions of the present disclosure are that they provide greater flexibility for the device. The flexibility can be provided about Y axes 600 as shown in FIG. 14 for example. Or with the plate configuration of FIG. 15A about X axes 610 and Y axes 620.

Referring back to FIG. 3 additional layers are the lower Mylar sheet 650 with openings and the TEC Assembly 670. As shown the TEC Assembly can include a TEC, the previously-mentioned copper squares, the copper bus line and wires. Thermistors are also shown in the figures.

A core composite layer 800 has holes 810 cut in it. The upper Mylar sheet 830 also has holes 840 cut in it for the TECs. The top plate is shown at 850 and the biocompatible layer at 860.

Referring to the cross-sectional views the adhesive for attaching the TEC's to the plate pieces (bottom plate) is shown and the thermal paste/epoxy for attaching the TECs to the top plate is shown. And the threads or other mechanical connect are shown.

2. Construction and Operation of Control Console and Umbilical

2.1 Control Console Construction

The control console can be comprised of the following components:
- (a) Enclosure
- (b) Quick-disconnect fittings
- (c) Power and signal plug
- (d) USB port
- (e) ¼" Jack
- (f) AC Power inlet
- (g) Fan(s)
- (h) Radiator
- (i) Pump
- (j) Reservoir
- (k) Flow meter
- (l) Level sensor
- (m) AC to DC power supply
- (n) Battery
- (o) DC to DC power supplies
- (p) H-Bridge
- (q) Microcontroller printed circuit board assembly (PCBA)
- (r) Screen driver board
- (s) Touch screen

2.1.1 Enclosure

The enclosure can be manufactured from laser cut acrylic, cast urethane, injection molded plastic or a similar method. It can be made from a single piece or by joining multiple panels that are either snapped together, screwed together, or by other mechanical or adhesive methods including a combination of the methods. The enclosure's main purpose is to house the internal components of the control console as well as mount the input and output ports and connector needed to interface with the umbilical and therefore HEMs. This enclosure can also maintain its rigidity with vents, for heat dissipation. The enclosure also can be constructed to maintain safety in the event of a fluid leak near electrical components.

2.1.2 Input and Output Components

The input and output components can be panel mounted to interface with a plug, cable, or tube. They can be installed by creating a cut-out in the enclosure of the specified component, such that it can be inserted partially through the hole and mechanically fixed, whether through screws or a snap-in feature. The quick disconnect fittings, the power and signal plug, the USB port, the ¼" jack, and power outlet are all installed in this manner. The touch screen is installed in a similar manner but rather than being put through the enclosure, it is mounted such that the profile cut out of the enclosure allows access to the screen without the part extending out.

2.1.3 Internal Components

The internal components are all mounted by screw mounts or affixed to platforms with various mechanical or even adhesive methods. The fan(s) are mounted to the radiator, and the radiator fan system is mounted such that the fans directly come into contact with a vent, and they are screw-mounted into place. The pump, AC to DC power supply, necessary DC to DC power supplies (zero to two depending on the design), H-Bridge, microcontroller PCBA, screen driver board are all screw mounted. The reservoir is held in place by being mounted on a shelf or platform.

2.1.4 Electrical System

The AC to DC power supply and battery provide power to all the components in the system. They are installed such that when the device is plugged into a power source the battery is charging, and when the device is unplugged the device operates on the battery. Depending on the design and component power needs, there are additional DC to DC power supplies that are powered by the power supply or battery. This collection of power supplies and battery are referred to as the power supply system. The power outlet is then wired with 600V rated cable to the power supply system. The power supply system is then distributed to the appropriate components via wiring. The components that require power include the fan(s), the pump, the H-Bridge, the microcontroller PCBA, and in some designs, the screen driver board and touch screen may need individual power. There are additional electrical interconnections separate from the power supply system. Wiring is necessary between the power and signal plug to the H-Bridge and to the microcontroller PCBA. Additional wiring is necessary from the USB port, ¼" jack, flow meter, level sensor, H-Bridge, and screen driver board to the microcontroller PCBA. There is also a wiring connection needed between the touch screen and the screen driver board. All this wiring is completed via screw terminals, soldering, crimping, or plugs, depending on the components specification.

2.1.5 Fluid System

The fluid system within the enclosure is all interconnected with ⅜" or ¼" diameter flexible tubing, such as PVC or polyurethane. They are connected to the individual components using barb or compression fittings. They can be straight or angled, and are screwed into the components. The tubing is connected from the reservoir to the pump inlet and from the pump outlet to the outlet quick disconnect fitting, where the umbilical is attached. The tubing also goes from the inlet quick disconnect fitting to the radiator and from the radiator back into the reservoir. Between the pump outlet and before the outlet quick disconnect fitting, the flow meter is installed with the same barbed fittings. In addition, a second threaded hole is created in the reservoir so that the level sensor can be installed.

2.2 Umbilical Construction

The umbilical is an extended section of a paired tube, such as PVC or polyurethane, as well as an extended piece of wiring assembly between ⅓ of a meter to four meters. There are two tubes for the fluid, again either ⅜" or ¼" in diameter and made from a flexible material, that go from quick disconnect fittings of the control console to the HEM. The appropriate connector, with barbs if necessary, are attached to the ends of these tubes such that it can plug into the quick disconnect fittings and into the HEM. The wire assembly is comprised of two cables capable of carrying current to the HEMs and at least two wires that can bring signals from the HEMs temperature probe. Additional wires are included if there are more than one temperature probe being used in the HEM. The cables and wires are crimped and soldered appropriately in order to be connected to the terminal of the plugs that goes into the control console on one end and into the HEM on the other end. A braided sleeve or other sheathe is then wrapped around the entire cable and tube assembly.

2.3 System Operation

The touch screen is interfaced by the user and in the simplest case a single temperature below room temperature is set for an indefinite amount of time (it will be possible for the user to set and use or select programmed temperature and time. algorithms). The microcontroller receives the temperature signal from the HEM. It responds by transmitting the appropriate signal to the H-Bridge which then, powered by the power supply system, can produce and send the necessary power to the HEM through the umbilical assembly. This allows the HEM to approach the set temperature. This feedback loop is repeated as necessary to maintain the user's selected temperature. In conjunction, the heat created by the HEM is being removed via the fluid system. Fluid is continuously flowing in a closed loop. The pump is drawing fluid from the reservoir and sending it through the umbilical into the HEM where it collects heat and returns via the umbilical. It then passed through the radiator and returns to the reservoir. When passing through the radiator, the collected heat is dissipated from the air forced through the radiator by the fans. The fans also help to remove excess heat produced from the electrical components in the enclosure.

3. Heat Exchange Module Construction

Discussed below are the components and fabrication process for the Heat Exchange Modules (HEM) of this disclosure, which can be adapted and used in a heat exchange system of the present disclosure for example. Generally, there are two methods of fabrication for the module, whose differences are described in detail later in this disclosure. The fabrication process set forth below is in the order that components appear in first fabrication method.

3.1 Water Circulation

The circulation of water throughout the device is essential in extracting heat from the HEM. The water circulation is done through two sheets of thermoplastic polyurethane (TPU), or other similar material that can be RF welded (or similar process) into channels for water to flow through. TPU material is used because it is thin, flexible, and can be easily manufactured to specification.

3.2 RF Weld

The design of the RF weld is custom to the specifications of each different HEM. Aside from a typical welding design of a typical HEM, and another possible design is shown. Each TPU sheet is a thickness of 15-40 mils (to be decided), and the RF weld line is three mils (subject to change). TPU inlets/outlets (typically in the form of elbows) are also RF welded at the ends of the designed water channels to allow the inlet and outlet of the water to be circulated. These inlets/outlets vary in size and have an inner diameter (ID) of either ¼" or ⅜" depending on the specifications of each HEM. The system of the two TPU sheets and elbows welded together will hereby be referred to as the 'water channels.'

3.3 'Windows' in the TPU Sheet

Since the TPU is not thermally conductive, an opening must be created in the water channels to allow for sufficient transfer of heat into the water from the device. The TPU sheet that does not have the elbows RF welded to it is cut in the shape of rectangles to form 'windows' in it. This is typically done via die-cutting, but can be done by other methods. A number of the figures show the water channels with windows cut out. This figure shows only one of the many possible configurations of the windows cut in the TPU sheet. In reality, the number of windows can range from one large window to as many windows as there are TECs in the device. The higher number of windows, the more flexible the device can be. This will be further explained below.

3.4 Thermally Conductive Layer ('Bottom Plate')

With an opening now in the water channels, a thermally conductive material must be used to seal the water channels to prevent leaking. This material is typically a thin metal plate, either copper or aluminum of thickness 7-12 mils (to be determined), but can be any semi-flexible thermally conductive substrate. The metal plate is cut into pieces that are relatively larger than the window cutouts in the TPU (usually by ~10 mm). The reason a single large piece of metal is not used is to allow for flexibility in the device and to reduce weight. The areas in between the metal plates allow for more flexibility in the device, since the TPU is much more flexible than the metal. Revisiting the windows discussion earlier, the number of metal plates is the same as the number of windows cut out in the water channels. For instance, a small window can be cut around each TEC (twelve windows total), and twelve metal plates, each a bit bigger than the size of the windows, can be used to seal each window. This method would allow for more flexibility since it would have flexibility along two axes instead of just one Because all of these plates lie within the same plane, and for ease of discussion, they will collectively be referred to as the 'bottom plate'. This plate may also be referred to as the 'hot plate', since during normal cooling operation this plate will heat up, whereas the 'upper plate' (discussed later) will be cold. (The bottom plate can be broadly referred to as a 'cover').

3.5 Sealing the Water Channels to the Thermally Conductive Layer

Figure 11:
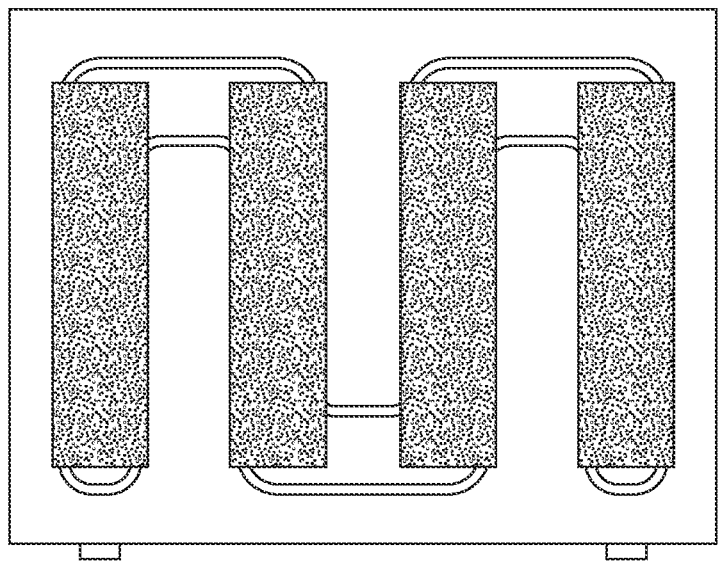
FIG. 11 is a view similar to FIG. 10 showing thermally conductive plates covering the windows.
Figure 13:
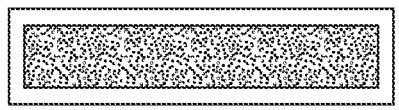
FIG. 13 is an enlarged plan backside view of one of the plates of FIG. 12A depicting the adhesive around the perimeter of the plate.

The sealing process involves the use of either a structural adhesive (typically either epoxy or acrylic), or a pressure sensitive transfer tape. Examples include: Devcon HP250 (acrylic adhesive), 3M DP8005 (epoxy adhesive), and 3M 9472 (transfer tape). For these adhesives, both the TPU and metal plates must be thoroughly abraded and cleaned to allow for proper bonding. The adhesive or tape is placed on each plate in the areas that overlap the TPU, but not in areas where water will contact the plate. Putting adhesive over the whole plate would both waste material and form an unwanted barrier that heat must transfer through to reach the water. FIG. 13 shows adhesive laid onto the plate. The rectangles with adhesive are set to the TPU and allowed to cure, sealing the water circulation channels. FIG. 11 shows the plates bonded to the TPU sheet. FIG. 12A shows the metal as transparent to see the windows below. In the Second Method this sealing process can be completed after the rest of the device has been assembled (see below).

3.6 Heat Transfer Elements (TECs)

Figure 16:
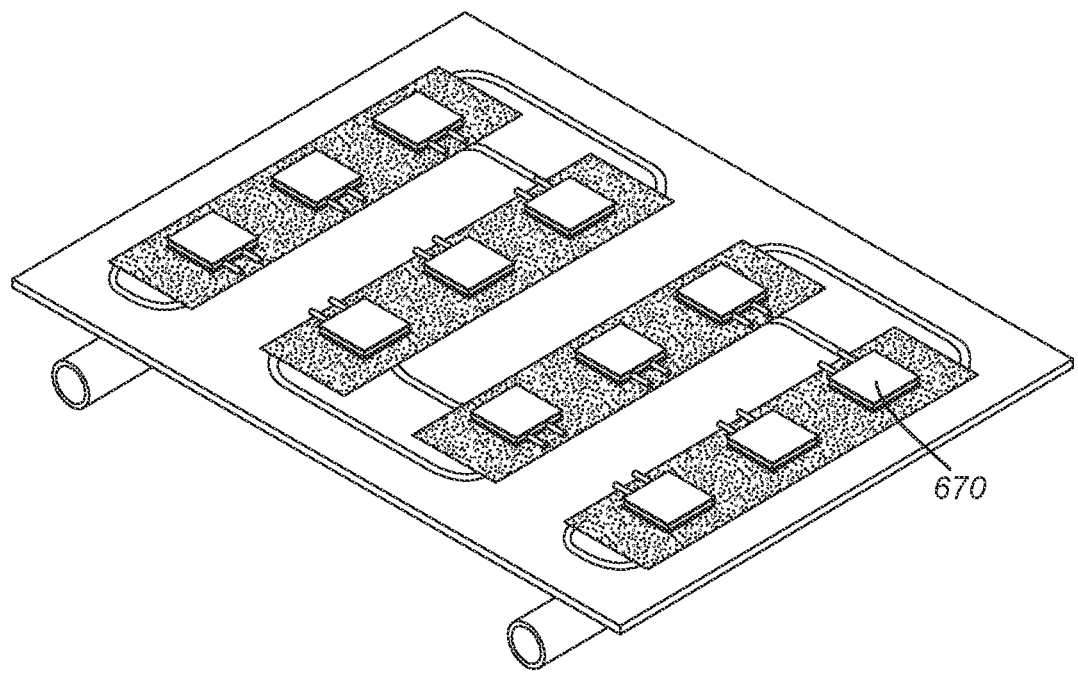
FIG. 16 is a view similar to FIG. 11 and showing the thermoelectric cooler (TEC) assembly in place on the plates.
Figure 17:
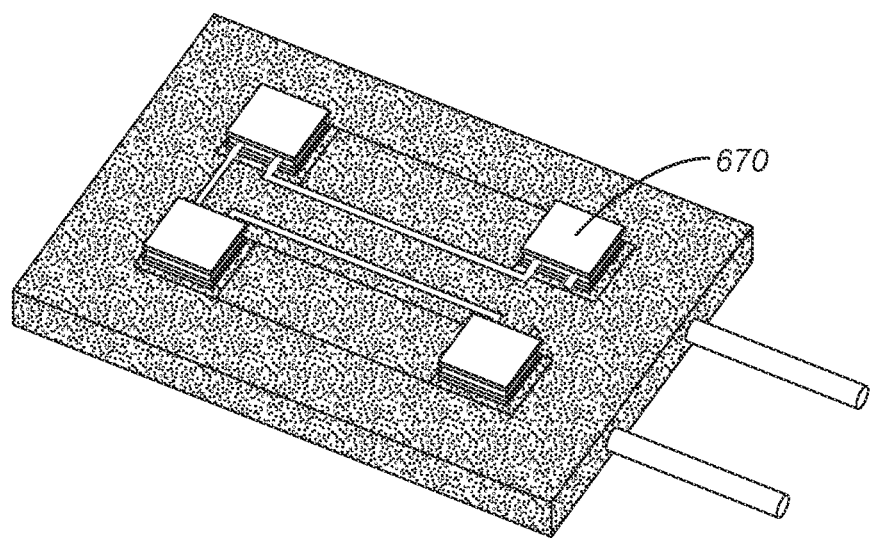
FIG. 17 shows in perspective an alternative TEC assembly and thermally conductive plate arrangement with the details of the TEC assembly.
Figure 18:
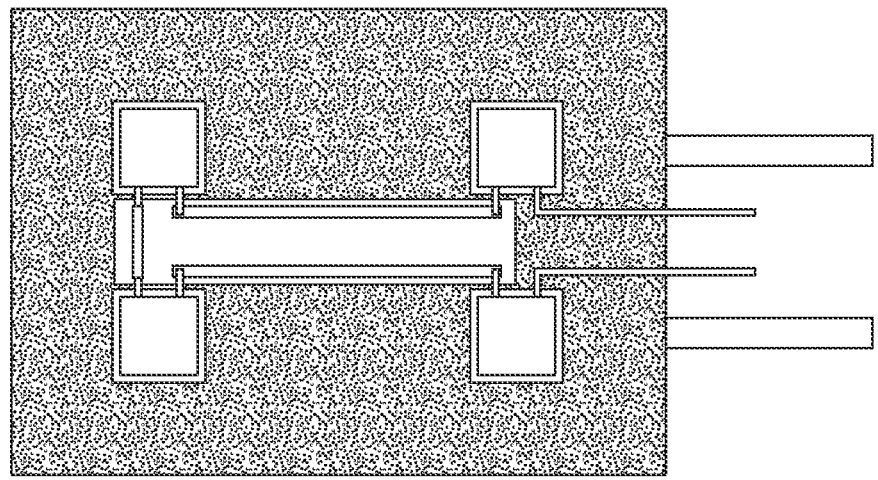
FIG. 18 is a top plan view of FIG. 17.

The next step is to arrange the modules that produce the cooling effect in the device, the thermoelectric coolers (TECs). The TECs operate on electrical power, so they are connected to a power source via bus bars. These bus bars are made of copper, thin, flexible, and keep a low profile inside the HEMs. The low profile is essential in maintaining interstitial space within the HEM between the two sides of the TECs. The bus bars are highly electrically conductive, which prevents them from heating up. Any heat generated through resistance losses in the wiring would inherently cause the HEM to be less efficient. The wiring on each TEC is trimmed down to about ¼". Copper bus bars are cut to the corresponding lengths between TECs, and the TEC wires are soldered to the bus bars. If the HEM has multiple banks, the bus bars are soldered together at junctions. Each TEC is cleaned thoroughly with acetone upon completion of soldering. This completes the 'TEC chain.' To prevent shorting the circuit, insulating tape is placed on the bottom plate in any area the bus bar may come in contact with the plate. FIG. 16 and FIG. 17 illustrate the TEC assembly with TECs 670.

FIG. 12B is a view similar to FIG. 12A showing the backside of the channel assembly but with the alternative embodiment in which the windows are not cut out, keeping the water channel layer intact.

FIG. 15B is a view similar to FIG. 15A but of an alternative embodiment connecting the twelve plates with another cover represented here by a hashed pattern. This cover can be a meshed material, a material with perforations along the axes of flexibility, such as a perforated foil, or a cover with varying thickness, such as a foil that is thinner along the axes of flexibility, all of which would connect the plates and still provide the axes of rotation for flexibility. It is also possible to do this with four plates or any other number of plates necessary to meet the design requirements.

3.7 Body-Facing Interface Layer ('Top Plate')

This layer can be a thermally conductive metal plate (but can be any semi-flexible thermally conductive substrate) that will be placed on the opposite side of the TECs. This is referred to as the 'upper plate' or 'cold plate'. A thermistor is added to this plate to measure the temperature of the surface that is in contact with the skin. To do this, the thermistor is placed in a suitable location (typically the middle of the plate) and the insulated lead wires are taped to the plate using thermally resistant tape. A thermally conductive adhesive (typically Dow Corning 3-6750) can be then placed around the thermistor, just enough to cover it completely. The adhesive can be cured to set the thermistor in place.

3.8 Insulation in the Interstitial Space ('Core Composite')

Figure 19:
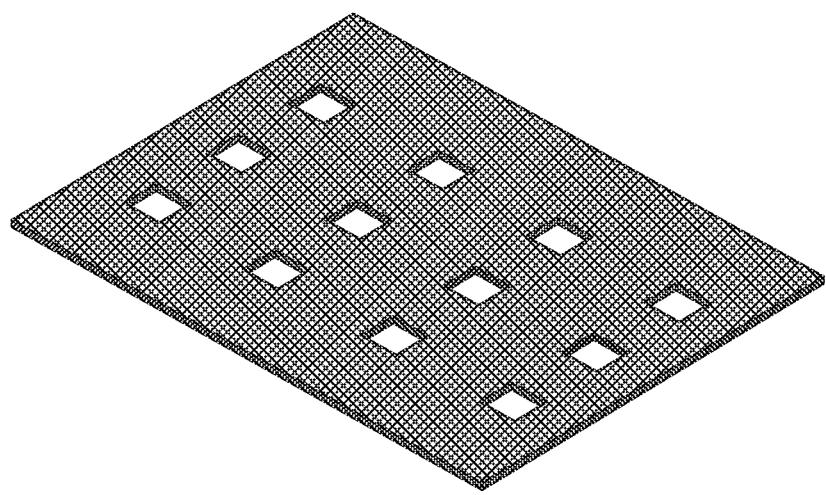
FIG. 19 is perspective view of a core composite layer of the module shown in isolation and before configuring.
Figure 20:
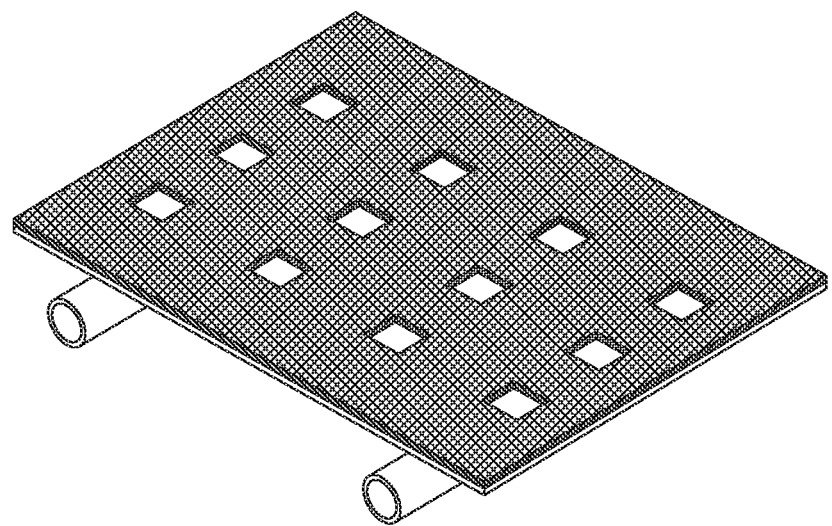
FIG. 20 is a perspective view similar to FIG. 16 with the core composite layer of FIG. 19 configured and in place.
Figure 21:
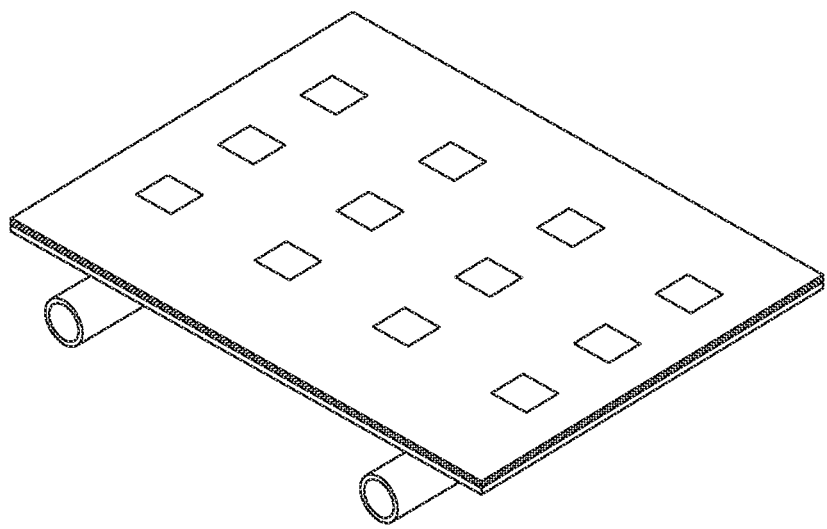
FIG. 21 is a view similar to FIG. 20 with the upper Mylar sheet in place on top of the core composite layer.
Figure 22:
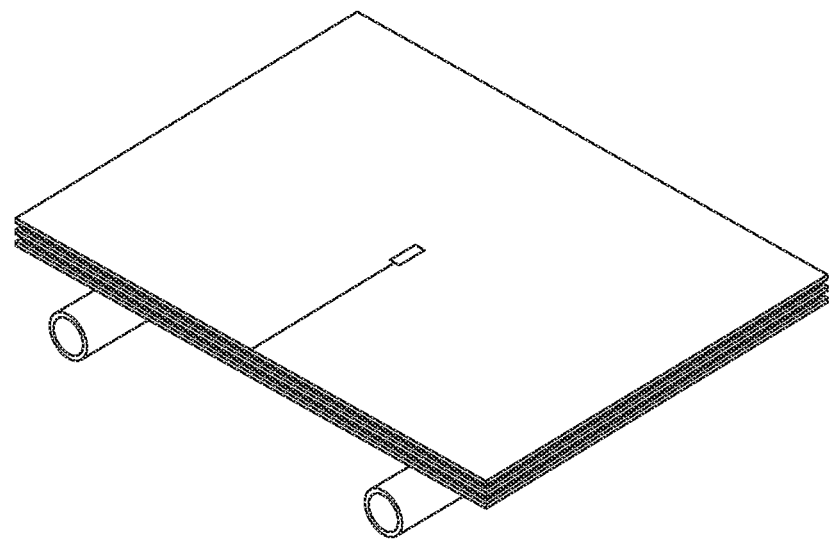
FIG. 22 is a view similar to FIG. 21 with the top plate in place.
Figure 23:
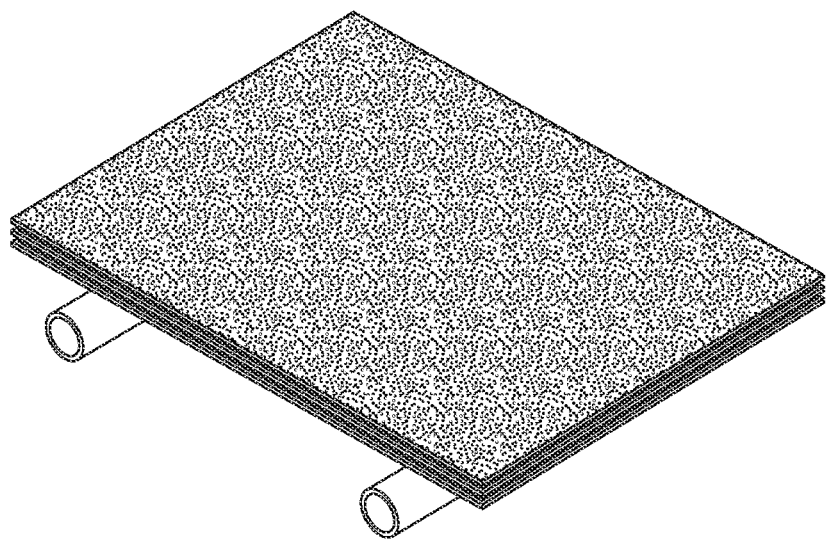
FIG. 23 is a view similar to FIG. 22 with the biocompatible layer in place.

The interstitial space is defined as the area between the top and bottom metal plates that is not taken up by the TECs or other elements (thermistor, bus lines, etc.). A material called a 'core composite' is used, and examples are Koroyd or Amarid Honeycomb. These are structured materials often shaped as a honeycomb with empty cells. See FIG. 19. The core composite can be used instead of, for example, a silicone foam. The core composite is cut in the areas where the TECs are present to fill all but those areas between the two metal plates (interstitial space). The material is a good thermal insulator because there is air in every core cell, minimizing the amount of heat transfer through material in contact with both plates. The core composite also maintains its structure over time, keeping the separation of the top and bottom plates, for thermal insulation. The core composite advantageously does not condense or compress over time, which would allow the plates to merge closer to each other. The core composite also maintains the structure of the HEM during the mechanical fastening process, preventing the plates from compressing into each other.

In addition, a sheet of Mylar or similar reflective material can be placed on the either side of the core composite for further insulation. These sheets prevent heat from radiating between the two plates by reflecting any emitted radiation back to the plate from which it originates.

3.9 Device Assembly

The assembly of the device can use a thermally conductive epoxy to adhere the TECs between the two metal plates, or preferably a thermal paste (typically Arctic MX-4 Compound) that allows for some give between the TECs and the plates on either side of them. With a thermal paste used (instead of an epoxy, for example) a method is needed to hold the device together (basically creating a sandwich that holds the TECs in contact with the metal plates). The TECs maintain intimate contact with the metal plates, so that that there is sufficient heat transfer between the materials.

This method is mechanical fastening. The mechanical fastening may be sewing, use of rivets, or a similar procedure that will hold the device together structurally. This discussion will use sewing as the primary method, although others are just as viable. Two methods of mechanical fastening may be used, described in the following two subsections.

3.9.1 First Method

This layer assumes that all of the aforementioned procedures have been carried out, and that the bottom plate is attached and sealed to the water channels at this point. The TEC chain that was produced earlier is now used. A thin layer or bead of thermally conductive paste is placed onto the "top" surface (the surface to be in contact with the top plate) of each TEC. The chain of TECs is then placed on the top plate. The first sheet of Mylar is then placed over the top plate around the TECs. The core composite is then placed over the Mylar sheet and around the TECs. The second Mylar sheet is then placed over the core composite and around the TECs. A thin layer or bead of thermally conductive paste is placed onto the 'bottom' surface (surface to be in contact with the bottom plate) of each TEC. The bottom plate is then placed on the TECs.

Recall that the bottom plate is already sealed to the water channels. At this point, the entire device is mated, and it just needs to be mechanically fastened.

Figure 25:
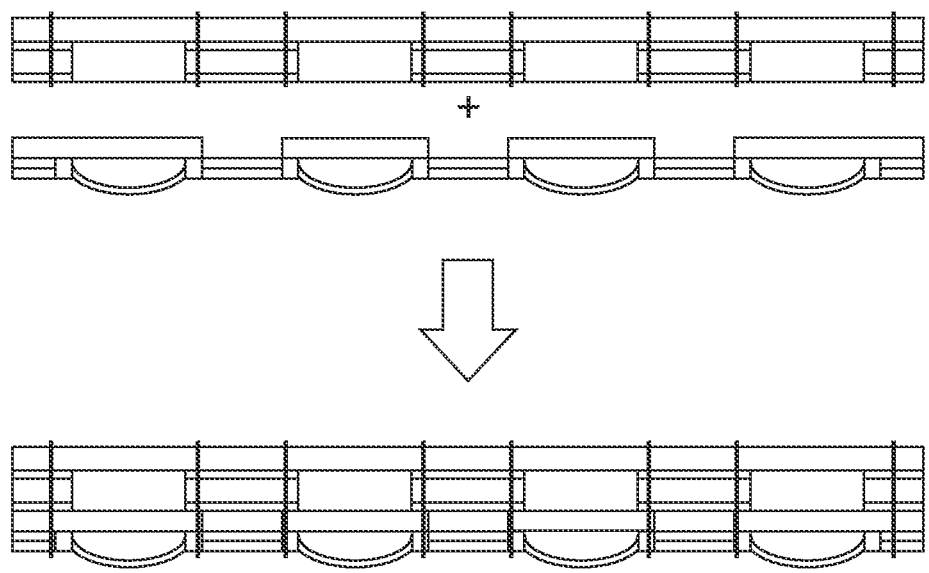
FIG. 25 is a view similar to FIG. 24 showing an alternative second method of mechanically securing the heat exchange stack together with the mechanical securement extending through the channel assembly.
Figure 26:
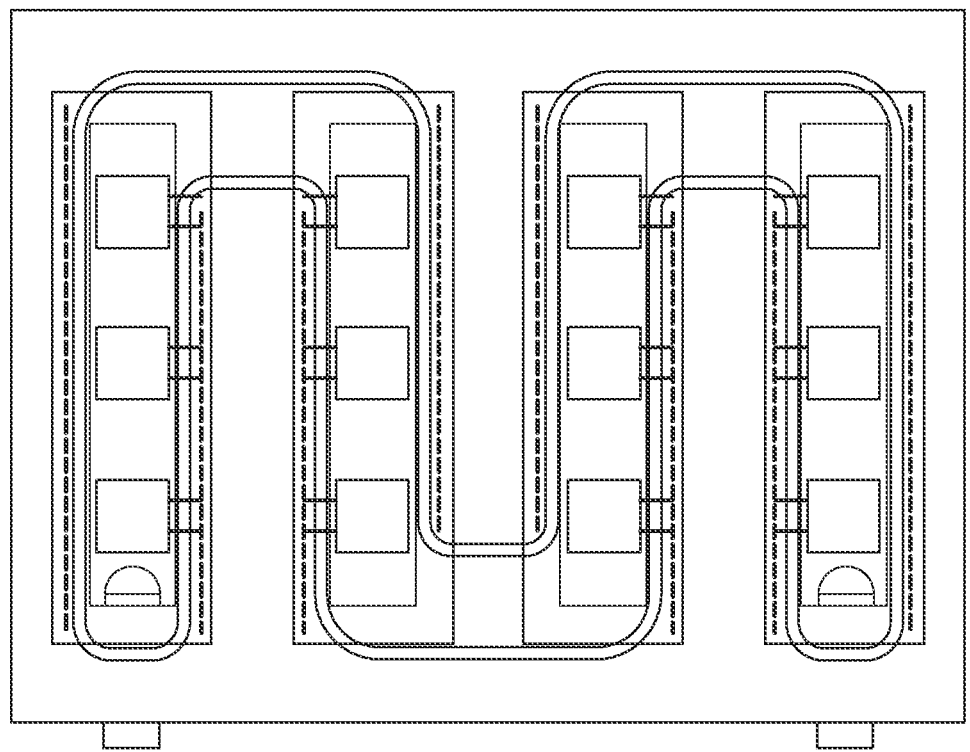
FIG. 26 is a top plan view similar to FIG. 16 but showing the areas of mechanical securement of the method of FIG. 24.
Figure 27:
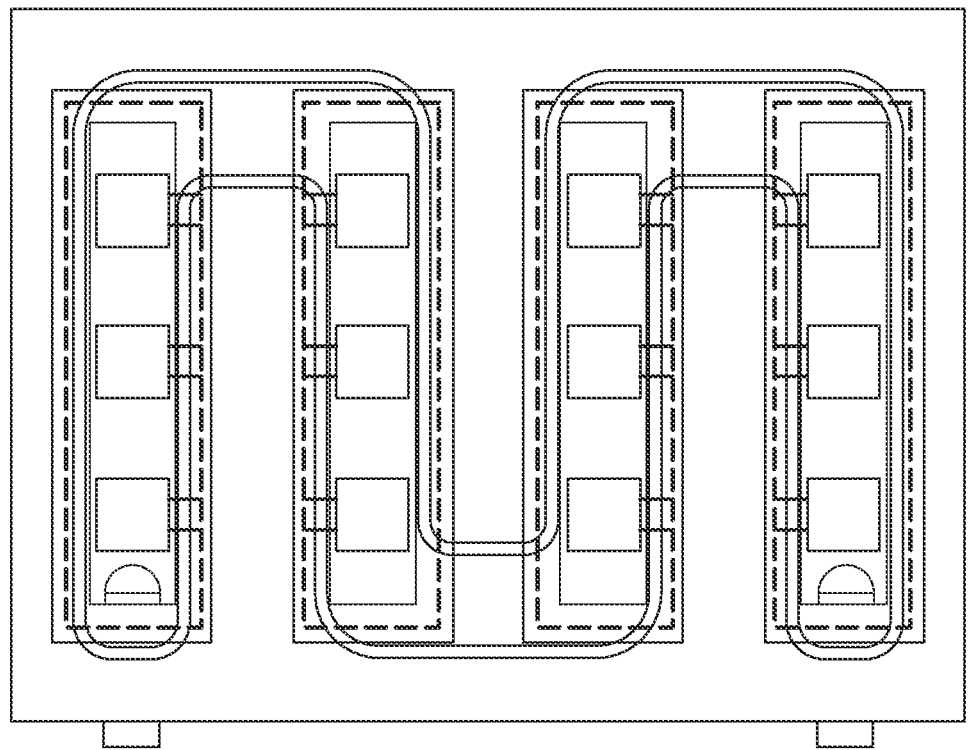
FIG. 27 is a top plan view similar to FIG. 16 but showing the areas of securement of the method of FIG. 25.

All of the components are held in place with c-clamps or similar jig, and the entirely of the device is passed through a sewing machine. The thread therefore penetrates through the entirety of the device. It is important to note that the thread can only be in certain locations. It may not pass through in any location where the water is flowing, or else it was pierce the water channel and cause a leak. It also must pass through both bottom and top plates to hold them both together. This leaves the same area that the adhesive was placed on the bottom plate to seal it to the TPU for stitching See FIG. 25 for a cross-sectional view of the First Method.

3.9.2 Second Method

The main difference between the two methods is how many components the thread (or fastener) will pass through. In the second method, the device is fabricated in a different order, in which the sewing is not the last step, and therefore the thread does not have to pass through the entire device. In this method, what we will now define as the 'heat exchange stack' or HES will be made first. Making the HES follows the same exact procedure as the First Method, the only difference being that the bottom plate is not yet adhered to the water channels. Taking the procedure above for clarity:

The TEC chain can be as follows. A thin layer or bead of thermally conductive paste is placed onto the 'top' surface (surface to be in contact with the top plate) of each TEC. The chain of TECs is then placed on the top plate. The first sheet of Mylar is then placed over the top plate around the TECs. The core composite is then placed over the Mylar sheet and around the TECs. The second Mylar sheet is then placed over the core composite and around the TECs. A thin layer or bead of thermally conductive paste is placed onto the 'bottom' surface (surface to be in contact with the bottom plate) of each TEC. The bottom plate is then placed on the TECs.

The bottom plate in this method can simply be a piece of metal, with the water channels not yet adhered. Each metal plate can be sewn individually to the HES similarly to First Method.

Figure 24:
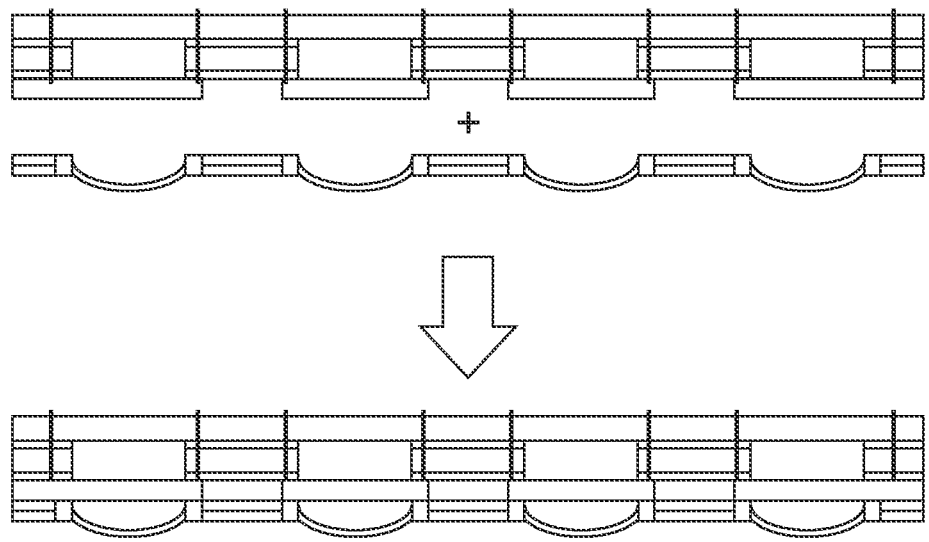
FIG. 24 is a stylized cross-sectional view through a module of the disclosure showing a first method of mechanically securing the heat exchange stack together with the mechanical securement not extending through the channel assembly.

After each bottom plate is sewn to the top plate, the HES is completed. The remaining step is to adhere the water channels to the bottom plate. The water channels with windows are made the same as described earlier, and they are adhered to the bottom plate in the same way, the only difference that the bottom plate is already attached the HES on the other side. See FIG. 24 for a cross-sectional view of the Second Method.

3.10 Biocompatible Layer

Figure 4:
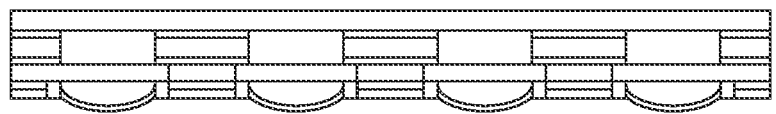
FIG. 4 is a stylized cross-sectional view of the module of FIG. 2.
Figure 5:
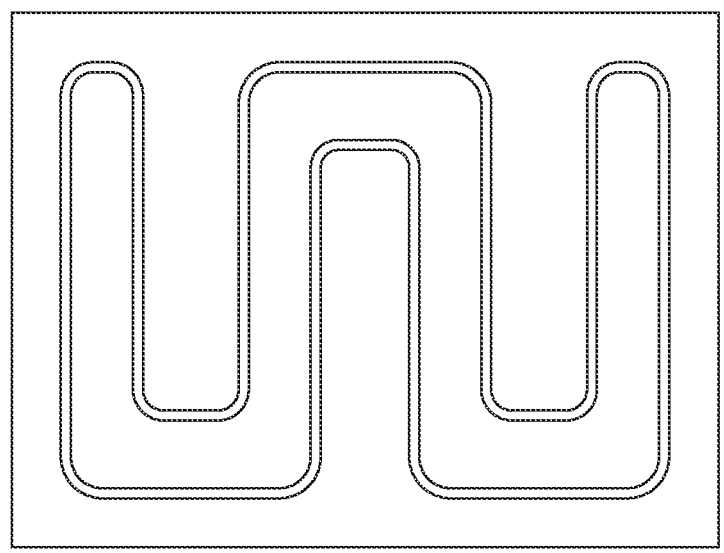
FIG. 5 is a plan view of a channel design of a channel assembly of a module of the disclosure.
Figure 6:
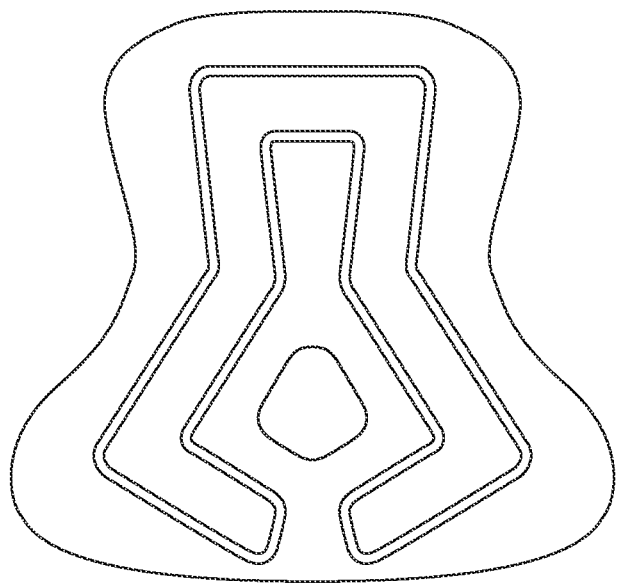
FIG. 6 is a view similar to FIG. 5 of an alternative channel design.
Figure 7:
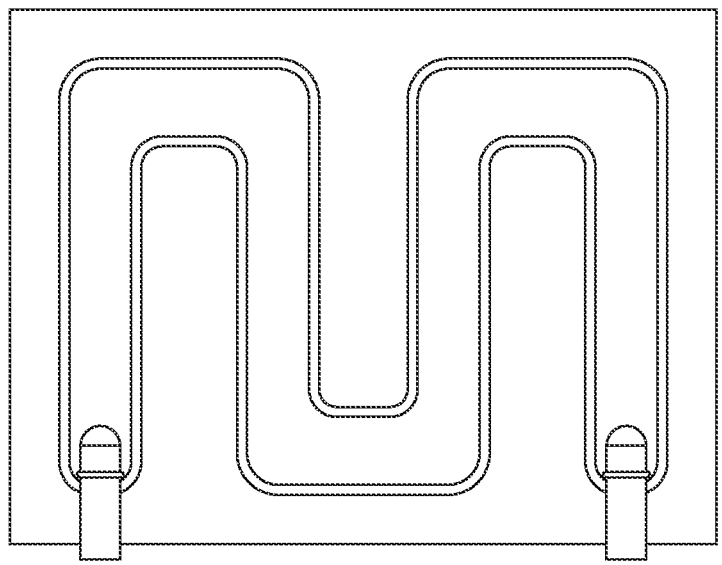
FIG. 7 is a top plan view of a channel assembly, such as that of FIG. 5, of a module of the disclosure.
Figure 8:
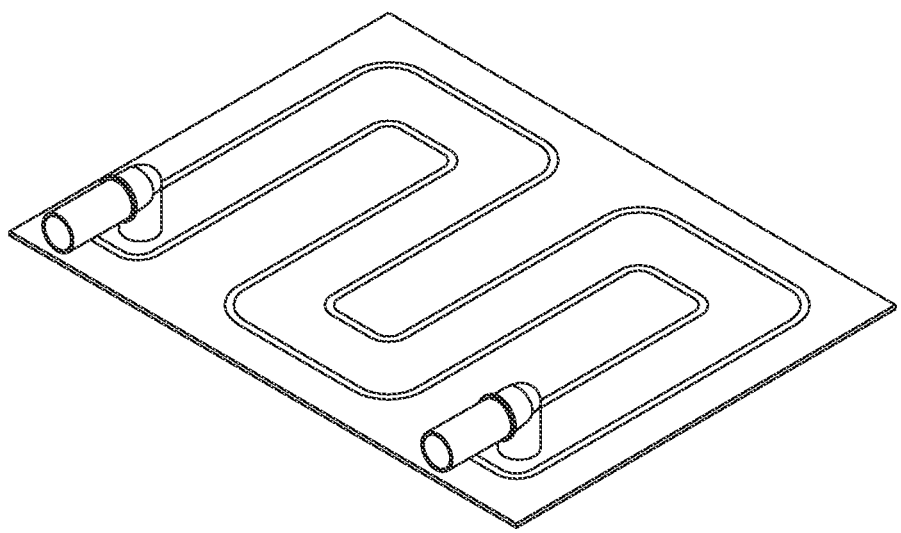
FIG. 8 is a perspective view of the channel assembly of FIG. 7.
Figure 9:
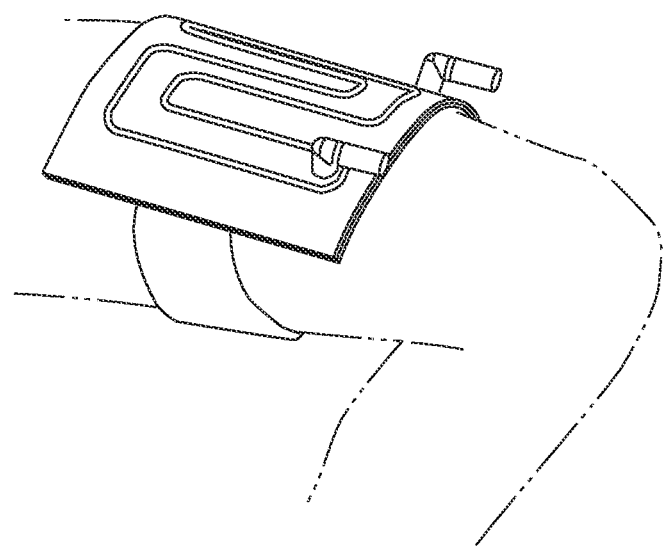
FIG. 9 is a perspective view of the module of FIG. 7 illustrated in a strapped position to a leg of a patient.
Figure 10:
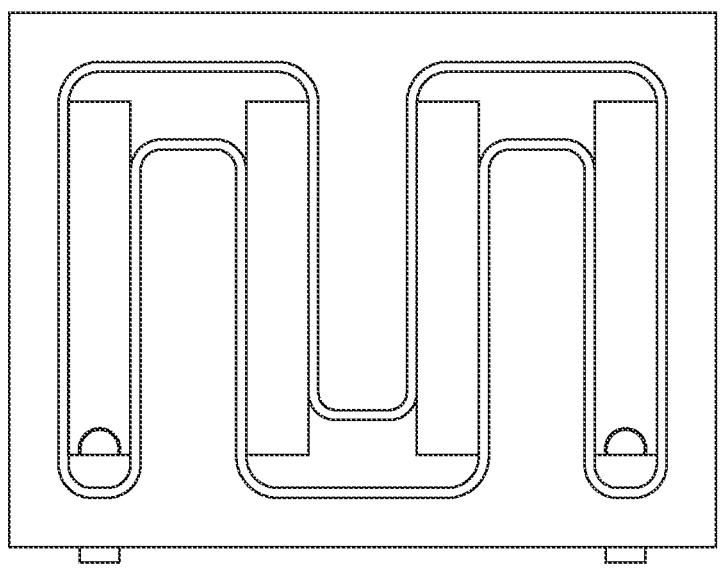
FIG. 10 is a top view of a channel assembly showing the channel windows.

A final step in completing the cooler is adding a thin layer (0.2 to 1 mm) of thermally conductive biocompatible material to the top plate. This material acts a buffer between the body tissue and the top plate so that the skin is not in direct contact with metal. Biocompatible materials include silicones for medical use, of which a variety are currently available. Alternatively, biocompatible skin adhesives, such as 3M 2476P, are also applicable. FIG. 4 shows the completed device, and FIG. 3 shows an exploded view of each layer.

4. Fabrication Procedure

As described above, there are two methods of fabrication. This section gives a succinct step-by-step procedure of both of these methods of the disclosure.

4.1 First Method
(a) A TPU sheet is die-cut to form windows in the material
(b) Inlet/outlet elbows are RF welded to a second TPU sheet
(c) These two sheets are RF welded together in a specified shape to form water circulation channels
(d) Bottom plates are cut to specification; the number of plates is equal to number of windows in TPU
(e) Adhesive is applied to the perimeter of the bottom plates and they are adhered to the TPU to seal the water channels
(f) TEC assembly is formed by soldering TECs together using copper bus lines
(g) Top plate, core composite and mylar materials are cut to specification
(h) Thermal paste is applied to upper side of TECs
(i) TECs placed against upper plate
(j) (Top) Mylar sheet added against upper plate, surrounding TECs
(k) Core composite added against Mylar sheet, surrounding TECs
(l) Second (bottom) Mylar sheet added against core composite material, surrounding TECs
(m) Thermal Paste is placed on bottom side of TECs
(n) TECs, along with upper plate materials in interstitial space, are placed against the bottom plate which already has the water channels adhered to it
(o) The HEM is mechanically fastened using sewing, the thread penetrating through the entire device 4.2 Second Method
(a) TEC assembly is formed by soldering TECs together using copper bus lines
(b) Top plate, core composite, and Mylar materials are cut to specification
(c) Bottom plates are cut to specification; the number of plates is equal to number of windows
(d) Thermal Paste is placed on upper side of TECs
(e) TECs placed against upper plate
(f) (Top) Mylar sheet added against upper plate, surrounding TECs
(g) Core composite added against Mylar sheet, surrounding TECs
(h) Second (bottom) Mylar sheet added against core composite material, surrounding TECs
(i) Thermal Paste is placed on bottom side of TECs
(j) TECs, along with upper plate materials in interstitial space, are placed against the bottom plate
(k) The HEM is mechanically fastened using sewing, the thread penetrating only through the HES assembly
(l) First TPU sheet is die-cut to form windows
(m) Inlet/outlet elbows are RF welded to second TPU sheet
(n) These two sheets are RF welded together in a specified shape to form the water channels
(o) Adhesive is applied to the perimeter of the bottom plates, which is already sewn to the rest of the HES, and they are adhered to the TPU to seal the water channels.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A heat exchange module, comprising:
a channel assembly including a channel, an inlet and an outlet;
a heat exchange stack attached to the channel assembly;
wherein said channel has a plurality of window openings configured to expose an interior of said channel;
the heat exchange stack including thermoelectric coolers (TECs);
the heat exchange stack including a thermally-conductive plate construction configured to provide flexibility for the channel assembly and thereby for the heat exchange module;

wherein the thermally conductive plate construction of the heat exchange stack includes thermally conductive plate pieces which are attached to seal each of said plurality of window openings to allow for transfer of heat into said channel;

a first heat reflective layer disposed over said thermally conductive plate pieces and said channel assembly, said first heat reflective layer having window cutouts through which each of said thermoelectric coolers pass to make thermal contact with one of said thermally conductive plate pieces;

a core composite layer disposed over said first heat reflective layer, wherein said core composite layer is configured with windows so that said core composite layer surrounds each of said thermoelectric coolers (TECs) to provide interstitial insulation;

a second heat reflective layer disposed over said core composite layer, said second heat reflective layer having window cutouts for each of said thermoelectric coolers (TECs);

a thermally conductive top plate disposed over said second heat reflective layer and configured to make contact with said thermoelectric coolers;

wherein a combination of said first heat reflective layer and said second heat reflective layer is configured to prevent heat from radiating between said thermally conductive plate pieces and said thermally conductive top plate by reflecting emitted radiation back to the plate from which it originates; and a thermally conductive biocompatible layer disposed over said top plate, said biocompatible layer configured to act as a thermal buffer between said thermally conductive top plate and body tissue to which said heat exchange module is applied.

2. The heat exchange module of claim 1, wherein the thermally-conductive plate construction includes flexibility along at least one axis.

3. The heat exchange module of claim 1, wherein said thermally conductive plate pieces comprise thin metal plates.

4. The heat exchange module of claim 1:
wherein said thermally conductive plate pieces are attached to seal each of said plurality of window openings utilizing a structural adhesive or a pressure sensitive transfer tape.

5. The heat exchange module of claim 1, wherein said thermally-conductive plate construction includes a flexible layer connecting the thermally-conductive plate pieces.

6. The heat exchange module of claim 5, wherein the flexible layer is a mesh, perforated material, or thinner material configured for increasing flexibility between a first thermally conductive plate piece and a second thermally conductive plate piece.

7. The heat exchange module of claim 1, further comprising a thermistor coupled to said thermally conductive top plate.

8. The heat exchange module of claim 1, wherein said windows of the core composite layer each comprise a pre-formed through-opening in which the thermoelectric cooler is positioned.

9. The heat exchange module of claim 1, wherein said heat exchange module is configured for connection to a console through an umbilical, and wherein fluid flow through the channel assembly and current supplied to the thermoelectric cooler (TEC) are controlled by the console.

10. The heat exchange module, of claim 1, wherein each of said thermoelectric coolers is adhered to one of the thermally conductive plate pieces and to the thermally conductive top plate by a thermally conductive epoxy or thermal paste.

11. The heat exchange module of claim 1:
wherein said first heat reflective layer and said second heat reflective layer comprises mylar sheet material.

12. The heat exchange module of claim 1, wherein said channel assembly comprises thermoplastic polyurethane (TPU).

13. The heat exchange module of claim 1, further comprising mechanical securement having a plurality of spaced mechanical fasteners, or sewing thread, which either passes through the channel assembly to the heat exchange stack, or that passes through the heat exchange stack and does not pass through the channel assembly.

14. The heat exchange module of claim 1, wherein said thermally conductive plate pieces are separated from one another to increase flexibility for the channel assembly and thereby for the heat exchange module.

15. The heat exchange module of claim 1, further comprising mechanically securing the heat exchange stack together, wherein the mechanical securement comprises sewing thread.

16. The heat exchange module of claim 1, further comprising mechanically securing the heat exchange stack together, wherein the mechanical securement comprises a plurality of spaced mechanical fasteners.

17. The heat exchange module of claim 1, further comprising mechanically securing the heat exchange stack together, wherein the mechanical securement passes through the channel assembly to the heat exchange stack.

18. The heat exchange module of claim 1, wherein a mechanical securement does not pass through the channel assembly and passes through the heat exchange stack.

19. The heat exchange module of claim 1, wherein said thermally conductive plate pieces are arranged in a row to provide flexibility about a Y axis in said heat exchange module.

20. The heat exchange module of claim 1, wherein said thermally conductive plate pieces are arranged in a two dimensional array in said heat exchange module to provide rotation flexibility along both X axis and Y axis.

* * * * *